(12) United States Patent
Lu et al.

(10) Patent No.: US 10,772,646 B2
(45) Date of Patent: Sep. 15, 2020

(54) METHOD FOR CONTROLLING HISTOTRIPSY USING CONFOCAL FUNDAMENTAL AND HARMONIC SUPERPOSITION COMBINED WITH HUNDRED-MICROSECOND ULTRASOUND PULSES

(71) Applicant: Xi'an Jiaotong University, Xi'an, Shaanxi (CN)

(72) Inventors: Mingzhu Lu, Shaanxi (CN); Yizhe Geng, Shaanxi (CN); Ruixin Li, Shaanxi (CN); Xuan Wang, Shaanxi (CN); Yanshan Liu, Shaanxi (CN); Dan Han, Shaanxi (CN); Yehui Liu, Shaanxi (CN); Yujiao Li, Shaanxi (CN); Rui Wang, Shaanxi (CN); Mingxi Wan, Shaanxi (CN)

(73) Assignee: Xi'an Jiaotong University, Xi'an (CN)

( * ) Notice: Subject to any disclaimer, the term of this patent is extended or adjusted under 35 U.S.C. 154(b) by 0 days.

(21) Appl. No.: 16/423,004

(22) Filed: May 25, 2019

(65) Prior Publication Data
US 2019/0307472 A1    Oct. 10, 2019

Related U.S. Application Data

(63) Continuation of application No. PCT/CN2016/113074, filed on Dec. 29, 2016.

(30) Foreign Application Priority Data

Dec. 19, 2016    (CN) .......................... 2016 1 1180724

(51) Int. Cl.
*A61B 17/22*    (2006.01)
*A61N 7/00*    (2006.01)
*A61B 17/00*    (2006.01)

(52) U.S. Cl.
CPC .......... *A61B 17/22012* (2013.01); *A61N 7/00* (2013.01); *A61B 2017/00172* (2013.01);
(Continued)

(58) Field of Classification Search
None
See application file for complete search history.

(56) References Cited

U.S. PATENT DOCUMENTS

2007/0083120 A1*    4/2007    Cain ................ A61B 17/22004
600/439
2009/0177085 A1    7/2009    Maxwell
(Continued)

FOREIGN PATENT DOCUMENTS

CN    1891167 A    1/2007
CN    104622525 A    5/2015

OTHER PUBLICATIONS

Vlaisavljevich, et al., "Histotripsy-Induced Cavitation Cloud Initiation Thresholds in Tissues of Different Mechanical Properties", IEEE Trans Ultrason Ferroelectr. Freq. Control 2014; 61(2): 341-352 (Year: 2014).*

*Primary Examiner* — Pascal M Bui Pho
*Assistant Examiner* — Farouk A Bruce
(74) *Attorney, Agent, or Firm* — Wayne & Ken, LLC; Tony Hom

(57) ABSTRACT

A method for controlling a histotripsy using a confocal fundamental and harmonic superposition combined with hundred-microsecond ultrasound pulses, including: 1) positioning a target tissue by a monitoring and guiding system and adjusting a position of the target tissue to a focal point of a transducer; 2) first stage: controlling the confocal fundamental and harmonic superposition combined with hundred-microsecond ultrasound pulses to form a shock wave in a focal zone; wherein a negative acoustic pressure exceeds a cavitation threshold; an inertial cavitation occurs
(Continued)

to generate boiling bubbles; the boiling bubbles collapse and achieve partial homogenization of the target tissue; 3) second stage: controlling the confocal fundamental and harmonic superposition combined with hundred-microsecond pulsed-ultrasound sequences to simultaneously irradiate a target zone and further mechanically disintegrate and homogenize the target tissue.

5 Claims, 19 Drawing Sheets

(52) U.S. Cl.
CPC ............... *A61B 2017/22009* (2013.01); *A61B 2017/22025* (2013.01); *A61N 2007/0004* (2013.01); *A61N 2007/0039* (2013.01); *A61N 2007/0065* (2013.01); *A61N 2007/0073* (2013.01)

(56) References Cited

U.S. PATENT DOCUMENTS

| | | |
|---|---|---|
| 2011/0251528 A1 | 10/2011 | Canney et al. |
| 2013/0090579 A1 | 4/2013 | Cain |
| 2015/0209602 A1 | 7/2015 | Slayton et al. |
| 2015/0258352 A1 | 9/2015 | Lin |

\* cited by examiner

METHOD FOR CONTROLLING HISTOTRIPSY USING CONFOCAL FUNDAMENTAL AND HARMONIC SUPERPOSITION COMBINED WITH HUNDRED-MICROSECOND ULTRASOUND PULSES

CROSS-REFERENCE TO RELATED APPLICATIONS

This application is a continuation of International Patent Application No. PCT/CN2016/113074, filed on Dec. 29, 2016, which claims the benefit of priority from Chinese Application No. 201611180724.4, filed on Dec. 19, 2016. The content of the aforementioned applications, including any intervening amendments thereto, are incorporated herein by reference.

TECHNICAL FIELD

The present disclosure is directed to focused ultrasound, and relates to a method for controlling a tissue ablation mode using a non-invasive focused ultrasound, and more particularly to a method for controlling a histotripsy using a harmonically related confocal pulsed focused ultrasound.

BACKGROUND OF THE INVENTION

High intensity focused ultrasound (HIFU) is a non-invasive therapy that focuses an ultrasound energy on a deep target tissue through a high-intensity focused-ultrasound transducer placed outside the human body so as to accurately damage the deep target tissue without damaging the tissue on the ultrasound path and the normal tissue surrounding the target zone. The thermal effect of ultrasound is mainly utilized in the traditional thermal ablation mode of HIFU. While, the histotripsy mode mainly utilizes the cavitation effect and mechanical effect of HIFU to disintegrate the target tissue into micron-sized fragments (homogenization for tissue cutting), which can be applied in tumor ablation. It can also be extended to applications such as therapies of kidney calculus, arrhythmia and thrombolysis.

Compared to the thermal ablation mode, the histotripsy has the following advantages. 1) The histotripsy overcomes the defects of the thermal ablation mode which is difficult to effectively damage adjacent tissues of great vessels due to the heat-sink effect, thereby increasing the effectiveness of the HIFU. 2) An absorbable liquid by tissue is formed after the therapy of the histotripsy mode. Compared to the coagulation damage generated in the thermal ablation, the liquefied target tissue is easy to be absorbed by periphery tissue, and the postoperative recovery is faster. The histotripsy is more suitable for clinical application. 3) The cavitation cloud and boiling bubbles generated during the therapy of the histotripsy can be monitored by B-mode ultrasonic device in real-time so as to conveniently evaluate the therapy process.

The existing histotripsy techniques mainly includes two modes, which are a histotripsy using an extremely high intensity ultrasound with a length of several-microsecond pulse train to generate cavitation cloud and a histotripsy using an ultrasound with a length of several-millisecond pulse train to generate boiling bubbles. The cavitation cloud histotripsy (CH) process needs to control the formation of shock wave in a focal zone, and the negative acoustic pressure is required to exceed the cavitation threshold. The shock wave is reflected by a single microbubble to form a large negative acoustic pressure, and is superimposed with an incident wave to form the cavitation cloud. A research team of the University of Michigan has proposed and developed a therapy model to homogenize soft tissue using an ultra-high intensity pulsed ultrasound to generate cavitation and mechanical effects. U.S. Pat. No. 6,309,355 B1 (Cain, titled "Method and assembly for performing ultrasound surgery using cavitation") disclosed a method for treating tissue lesion under ultrasound induction using a pulse sequence with a duration of less than 50 µs in 2001. Further, Cain (U.S. Pat. No. 8,057,408 B2, titled "Pulsed cavitational ultrasound therapy") proposed that the therapy process includes the subprocesses of initiation, maintenance, therapy, and feedback. The therapeutic parameters such as the acoustic pressure amplitude and duty cycle of the ultrasound and the pulse repetition frequency in the subprocess are controlled to produce different cavitation biological effects to improve the controllability of the cavitation cloud of the histotripsy mode. Further, Cain (US Application Publication 20130090579 A1, titled "Pulsed cavitational therapeutic ultrasound with dithering") proposed dissipating cavitation bubbles between two groups of pulses by a pulsed ultrasound with a duty cycle of less than 1%, thereby eliminating "cavitation memory". So that the distribution of cavitation bubbles in the focal zone is more random and the damage region is more uniform. Further, Cain (WO 2015027164 A1, titled "Histotripsy using very short ultrasound pulses") proposed a microtripsy method using very short ultrasound pulses of less than 2 cycles. The method increases the peak negative acoustic pressure to exceed the intrinsic cavitation threshold so as to generate a damage with a length less than one wavelength, and the damage region is precisely controllable. However, excessive acoustic pressure has an impact on the surrounding tissue, which puts pressure on clinical applications. The boiling histotripsy mainly uses an ultrasound with a length of several-millisecond pulse train to generate rapid heating boiling of the tissue, and when the boiling bubbles in the shockwave field, a strong mechanical action is generated to damage the tissue. Michael S. Canney, et al. (U.S. Pat. No. 8,876,740 B2, titled "Methods and systems for non-invasive treatment of tissue using high intensity focused ultrasound therapy") disclosed a method and apparatus for generating boiling bubbles in target tissue using an ultrasound with a length of several-millisecond pulse train. Khokhlova Vera, et al. (WO 2015148966 A1, titled "Boiling histotripsy methods and systems for uniform volumetric ablation of an object by high intensity focused ultrasound waves with shocks") disclosed methods and apparatus for guiding an ultrasound to generate boiling bubbles at different points of a target tissue for tissue lesion.

The synergistic mechanism by superposing two ultrasound waves with different frequency is also applied in ultrasound therapy. Kuang-Wei Lin (WO 2015138781 A1, titled "Frequency compounding ultrasound pulses for imaging and therapy") proposed a histotripsy method using a low frequency (100 kHz to 1 MHz) ultrasound and a high frequency (2 to 10 MHz) ultrasound to simultaneously act on a target tissue and controlling a pulse delay of two frequencies to form a unipolar pulse. G. Iernetti ("Enhancement of high-frequency cavitation effects by a low frequency stimulation" (Ultrasounds Sonochemistry, vol. 4, pp. 263-268, 1997)) utilized a high frequency ultrasound of 700 kHz and a low frequency ultrasound of 20 kHz to enhance cavitation effects. The low frequency ultrasound is used to amplify the cavitation effect of high frequency ultrasound at different cavitation stages in the target tissue region. The method of superposing the low frequency ultrasound to the high frequency ultrasound with frequencies of a kHz order has several shortcomings as follows. (1) The ultrasound with a frequency of a kHz order is large in volume of focal zone and cannot accurately damage the target tissue. (2) The ultrasound with a frequency of a kHz order has a low ultrasound amplitude in the focal zone and cannot effectively damage the target tissue.

The existing methods of histotripsy still have the following deficiencies. 1. The required peak acoustic pressure is large, and the cavitation cloud histotripsy (CH) requires a peak negative acoustic pressure of 15-25 MPa, and a peak positive acoustic pressure of greater than 80 MPa. The peak negative acoustic pressure required for boiling bubble (BH) is 10-15 MPa, and the peak positive acoustic pressure is required of greater than 40 MPa, which brings certain pressure on clinical safety. 2. The pulse duration of the cavitation cloud histotripsy is only about 10 μs, the duty cycle is about 1%, the ultrasound excitation time required for the formation of a lesion is longer, and the therapy efficiency is lower. 3. The shape of the lesion formed by the boiling histotripsy is difficult to control, usually resulting an excessive damage at a position of the near the transducer.

In view of the above deficiencies, a method for controlling a histotripsy using a confocal fundamental and harmonic superposition combined with hundred-microsecond ultrasound pulses is proposed to improve the efficiency and safety of the therapy.

SUMMARY OF THE INVENTION

The object of the present disclosure is to provide a method for controlling a histotripsy using a confocal fundamental and harmonic superposition combined with hundred-microsecond ultrasound pulses, which performs two stages of tissue lesion through a harmonic of a MHz order superimposed and hundred-microsecond pulsed sequence, thereby improving therapy efficiency and safety. In two stages of tissue lesion, two ultrasound waves of a MHz order are controlled to simultaneously act on the target tissue. The two ultrasound waves interfere and superpose in the focal zone as the amplitude and phase are adjusted, which form a higher peak negative pressure and promote the cavitation effect. Meanwhile, the two ultrasound waves do not superpose outside the focal zone. In addition, the present invention uses the fundamental and harmonic of a MHz order superimposed pulsed ultrasound to achieve the following purposes. (1) The fundamental and harmonic of a MHz order superimposed pulsed ultrasound can reduce the cavitation threshold and facilitate the formation of lesion when it is used to act on the target tissue. (2) The fundamental and harmonic of a MHz order superimposed pulsed ultrasound has a good confocal performance and the lesion formed is more precise and controllable. (3) The fundamental and harmonic of a MHz order superimposed pulsed ultrasound has a good thermal effect and can improve the therapy efficiency.

In order to achieve the above object, the technical solution is as follows.

A method for controlling a histotripsy mode using a confocal fundamental and harmonic superimposed hundred-microsecond ultrasound pulses, including:

1) positioning a target tissue by a monitoring and guiding system and adjusting a position of the target tissue to a focal point of a transducer;

2) first stage of lesion: controlling the confocal fundamental and harmonic superposition combined with hundred-microsecond ultrasound pulses to form a shock wave in a focal zone; wherein a negative acoustic pressure exceeds a cavitation threshold; an inertial cavitation occurs to generate boiling bubbles; the boiling bubbles in the shockwave field, and achieve partial homogenization of the target tissue;

3) second stage of lesion: controlling the confocal fundamental and harmonic superposition combined with hundred-microsecond pulsed-ultrasound sequences to simultaneously irradiate a target zone and further mechanically disintegrate and homogenize the target tissue.

Further, step 1) specifically includes the following steps: performing an image guidance and adjusting a spatial position of the target tissue to position the target tissue at the focal point of the transducer through a probe arranged in a center of the transducer.

Further, the transducer is a HIFU transducer.

Further, in step 1), choose respective cutting schemes in accord with its very size of the target tissue, the target tissue with a large volume (such as tumor) is cut out from a normal tissue along a conformal edge (histotripsy) of the target tissue; the target tissue with a small volume is directly liquefied.

Further, the transducer includes a fundamental array element and a harmonic array element, or fundamental array elements and harmonic array elements. In step 2), the pulsed focused ultrasound has a duty cycle (DC) range of 3%10%. The hundred-microsecond refers to a pulse duration of a single pulse within 100-1000 μs. A working frequency range of a pulsed focused ultrasound of the fundamental array elements is 1-3 MHz, and the working frequency range of the pulsed focused ultrasound of the harmonic array elements is 2-10 MHz. A pulse repetition frequency range is 20-900 Hz.

Further, the transducer includes a fundamental array element and a harmonic array element. In step 3), the pulsed focused ultrasound has a duty cycle (DC) range of less than 2%. The hundred-microsecond refers to a pulse duration of a single pulse within 100-1000 μs. The working range of a pulsed focused ultrasound of the fundamental array element is 1-3 MHz, and the working range of the pulsed focused ultrasound of the harmonic array elements is 2-10 MHz. A pulse repetition frequency range is 20-900 Hz.

Further, in steps 2a) and 3), a harmonic frequency is 2-10 times the fundamental frequency. An acoustic power of the harmonic wave is 0.1-1 times of an acoustic power of the fundamental wave. The fundamental wave and the harmonic wave have a phase difference of 0-360°, interfere and superpose in the focal zone.

Further, in a fundamental and second-harmonic superposition mode, the negative peak values of the fundamental wave and the harmonic wave superpose in the focal zone when the phase differences of the harmonic wave and the fundamental wave is 135°. The negative acoustic pressure achieves a maximum value under a phase control condition, which facilitates the formation of the cavitation. In a third-harmonic superposition mode, the negative peak values of the fundamental wave and the harmonic wave meet and superpose when the phase differences of the harmonic wave and the fundamental wave is 60°. The negative peak values achieve the maximum value after superposition. At the same time, the positive peak values of the fundamental wave and the harmonic wave also meet and superpose, such that the maximum value of the positive peak value is achieved, which facilitates the formation of the shock wave in the focal zone. The negative acoustic pressure exceeds the cavitation threshold and reaches the maximum value under the phase control condition, which is most conducive to the collapse of the transient cavitation bubbles.

Further, in steps 2) and 3), the absolute values of the negative acoustic pressures are both greater than 10 MPa and less than 15 MPa, and the positive acoustic pressure s produce the shock wave.

Further, the target tissue is taken from a sample of a phantom or ex vivo tissue.

Further, the transducer is a confocal spherical array element, including a fundamental array element and a harmonic array element, or fundamental array elements and harmonic array elements. The transducer has a hole in the center for placing the probe of the monitoring and guiding system. The transducer is a confocal sectorial split-array, confocal rectangular split-array, confocal annular split-array or confocal sector vortex split-array transducer.

Compared to the prior art, the present disclosure achieves the following beneficial technical effects.

The invention provides a method for controlling a histotripsy mode using a confocal fundamental and harmonic superposition combined with hundred-microsecond ultrasound pulses, which changes the viscoelasticity of the target tissue to form a loose structure by controlling a confocal fundamental and harmonic with a high duty cycle to superpose on the target tissue, achieving a preliminary homogenization of the target tissue. Then, the confocal fundamental and harmonic with a low duty cycle are superimposed on the target tissue to achieve complete homogenization. This mode control method can reduce the peak acoustic pressure required for tissue lesion histotripsy, reduce the impact on the surrounding tissues and improve the safety of therapy.

Further, the present invention adopts the fundamental and harmonic superposition combined with ultrasound pulses of a MHz order to act on the target tissue. The fundamental and harmonic superposition combined with ultrasound pulses of a MHz order has a better focusing performance and is more precise in lesion control than that of the harmonic superimposed ultrasound pulses of a kHz order. The harmonic superimposed ultrasound pulses of a MHz order has a better heat absorption performance when it irradiates the target tissue, which is more conducive to form cavitation clouds and improve the therapy efficiency.

Further, the present invention adopts confocal fundamental and harmonic superposition combined with ultrasound pulses to act on the target tissue. Specifically, two frequency waves simultaneously act on the target tissue. The amplitude and phase of the fundamental wave and harmonic wave are controlled to make the fundamental wave and harmonic wave interfere in the focal zone, to increases the peak negative acoustic pressure, which is more conducive to form the cavitation and improve the therapy efficiency. The fundamental wave and harmonics wave do not interfere outside of the focal zone, which reduces the impact on the surrounding tissues when the target tissue is treated and further improves the safety of the therapy. In addition, the confocal fundamental and harmonic superposition mode can effectively reduce the cavitation threshold of the focal zone and the impact on surrounding tissues, and improve the safety of the therapy.

Further, the present invention controls a single pulse duration to a few hundred microseconds, and set an off time between each pulse by controlling their duty cycle. This mode can limit the continuous and tempestuously growth of the cavitation bubbles, and weaken the shielding generated by the accumulation of cavitation bubbles at an end near the transducer to the subsequent shock wave, which makes the cavitation distribution more uniform, and the homogenization efficiency of the damage formed is higher. Based on the above three points, the present invention can effectively improve the therapy efficiency and enhance the therapy safety.

BRIEF DESCRIPTION OF THE DRAWINGS

In FIG. 1, the range of the off time T2 is 300-1200 ms, the range of the repetition numbers M is 50-500, the range of the repetition numbers N is 10-100, the range of the repetition numbers S1 is 4-20, and the range of the repetition numbers S2 is 8-30.

DETAILED DESCRIPTION OF EMBODIMENTS

The technical solution of the present invention will be further described below with reference to the accompanying drawings and specific embodiments.

In order to further improve the efficiency of histotripsy, the present invention proposes a method for controlling a histotripsy mode using a confocal fundamental and harmonic superposition with hundred-microsecond ultrasound pulses to improve therapy efficiency and safety based on the research and application status of the histotripsy technology. The method is divided into two stages of lesion. The first stage of lesion adopts a fundamental and harmonic superimposed-pulse sequence with a relatively high duty cycle. The higher the duty cycle, the longer the duration of the ultrasound pulse, and the more obvious the heat accumulation. In the first stage of lesion, the thermal effect and mechanical effect are used to achieve the purpose of generation of the inertial cavitation and boiling bubbles, and generates cavitation nuclei as much as possible to homogenize the target tissue. In the second stage of lesion, a fundamental and harmonic superimposed-pulse sequence with a relatively low duty cycle is used to further homogenize the target tissue while avoiding the thermal effect to impact the surrounding normal tissue.

In order to shorten the treatment time and promote the inertial cavitation and boiling effect, the present invention proposes a method for controlling a histotripsy mode using a confocal fundamental and harmonic superposition with hundred-microsecond ultrasound pulses, which is combined with a control method of harmonic frequency drive phase and a control method of harmonic frequency power to explore the optimal combination mode of the fundamental and harmonic superposition.

HIFU is mainly applied in the field of ultrasound therapy. However, the present invention studies the control method based on the phantom. Specifically, the present invention verifies and optimizes the model safety on the porcine liver, kidney and other in vitro tissues and on the living animals. Therapy of human diseased tissue is not directly involved.

Figure 3:
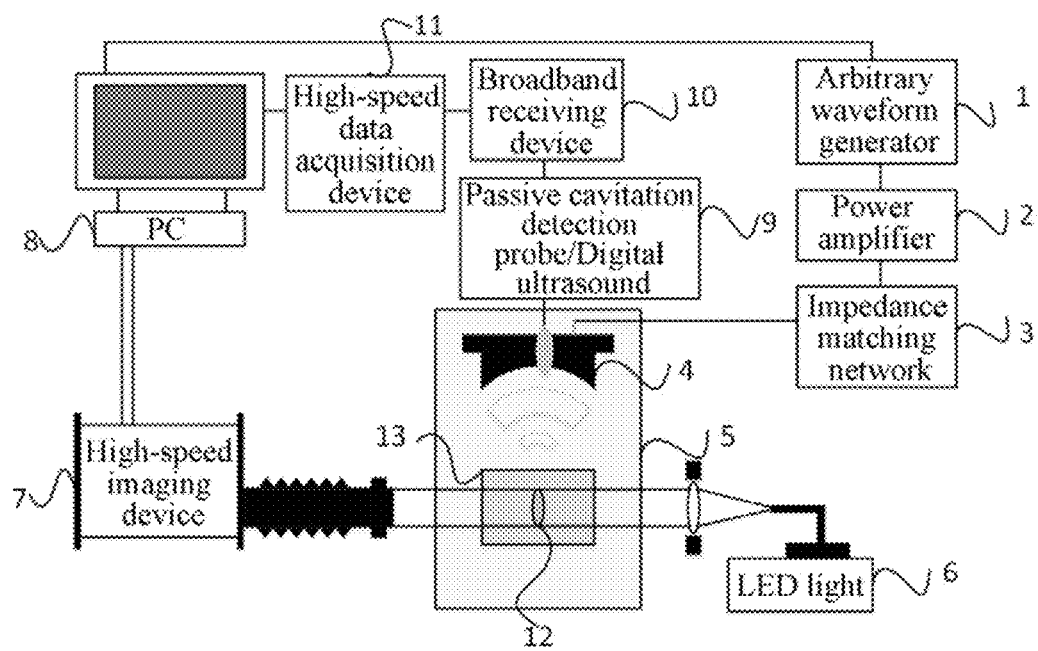
FIG. 3 is a block diagram of the method, where 1: arbitrary waveform generator, 2: power amplifier, 3: impedance matching network, 4: HIFU transducer, 5: water tank, 6: LED light, 7: high-speed camera, 8: PC, 9: passive cavitation detection probe or digital ultrasound, 10: broadband receiving device, 11: high-speed data acquisition device, 12: tissue target zone, and 13: sample.

Referring to FIG. 3, a system for implementing the method for controlling a histotripsy mode using a confocal fundamental and harmonic superposition with hundred-microsecond ultrasound pulses of the present invention includes a signal excitation module, a monitoring and guiding module, and a control module.

The signal excitation module includes an arbitrary waveform generator 1, a power amplifier 2, an impedance matching network 3 and a HIFU transducer 4, which are connected in sequence. The arbitrary waveform generator 1 is configured to generate a driving signal, which is amplified by the power amplifier 2 to a specified power and then connected to the HIFU transducer 4 by the impedance matching network 3.

The monitoring and guiding module mainly includes a passive cavitation detection probe (PCD probe) or a digital ultrasound 9, a broadband receiving device 10, a high-speed data acquisition device 11, an LED light 6 and a high-speed imaging device 7. The passive cavitation detection probe 9 is mainly configured to receive a passive cavitation signal of a broadband. The broadband receiving device 10 and the high-speed data acquisition device 11 are configured to evaluate the transient cavitation activity by collecting data. The high-speed imaging device 7 is configured to real-time monitor of the formation process of the lesion in the focal zone.

The control module includes a computer 8. The whole process of the experiment is digitally controlled by the computer 8. The computer 8 is connected to the high-speed imaging device 7 and the high-speed data acquisition device 11, and triggers the arbitrary waveform generator 1 and control its operation timing sequence.

The method for controlling a histotripsy mode using a confocal fundamental and harmonic superposition combined with hundred-microsecond ultrasound pulses of the present invention includes the following steps.

1) A target tissue 12 is positioned by a monitoring and guiding system (such as a digital ultrasonic imaging device), and a position of the target tissue is adjusted to a focus position of the HIFU transducer 4. An appropriate scheme is adopted according to a volume size of the target tissue. For a target tissue with a large volume size, the tissue edges are liquefied to cut out the target tissue. For a target tissue with a small volume size, the target tissue is directly liquefied.

2) The first stage is performed. A shock wave excited by the confocal fundamental and harmonic superposition combined with hundred-microsecond ultrasound pulse is used to form an inertial cavitation in the focal zone. The inertial cavitation and the boiling bubbles generated by the inertial cavitation cause the target tissue to form a loose partial tissue structure so as to achieve a partial homogenization and generate a large number of cavitation nuclei.

3) The second stage is performed. The confocal fundamental and harmonic superposition combined with hundred-microsecond ultrasound pulse is used to further mechanically disintegrate and homogenize the target tissue in the treated region, and finally achieve the efficient histotripsy.

In step 1), the histotripsy scheme is determined by analyzing the tissue volume in the target zone. For a target tissue with a large volume, a scheme of tissue cutting is adopted. Specifically, the focus point of the HIFU transducer is adjusted to target on the boundary between the target tissue and the normal tissue, the HIFU transducer is repeatedly moved to perform tissue lesionlesion multiple times so as to achieve the purpose of cutting the target tissue from the surrounding normal tissue. For a target tissue with a small volume, a scheme of direct damage is adopted. Specifically, the focus point of the HIFU transducer is adjusted to target on the target tissue, one or more tissue lesionlesions are directly performed.

Step 2) includes the following steps. The arbitrary waveform generator 1 transmits a pulse sequence with a relatively high duty cycle, which is amplified by the power amplifier 2 to a specified power. The HIFU transducer 4 is driven by the impedance matching network 3 and performs the first stage to the target tissue of sample 13 under monitoring of the monitoring and guiding system. The relatively high duty cycle (DC) range is 3%<DC<10%. The hundred-microsecond refers to a pulse duration within 100-1000 μs. An exciting pulse with an operational range of 1-3 MHz transmitted by one arbitrary waveform generator drives the fundamental array element after its power being amplified. An exciting pulse with an operational range of 2-10 MHz transmitted by another arbitrary waveform generator drives the harmonic array element after its power being amplified. At this stage, due to the characteristics of thermal and mechanical effects of the high duty cycle pulsed focused ultrasound, the inertial cavitation effect and boiling bubbles are generated in the target zone, thereby reducing the mechanical strength of the target tissue to achieve partial homogenization of the target tissue. At the same time, various kinds of mechanical actions such as inertial cavitation and shock waves form a large number of cavitation nuclei, which provide a damage basis for the second stage. Two harmonically related pulses intervene and superimpose in the target zone to form a shock wave and generate a higher peak negative acoustic pressure, which promotes the rectified diffusion of cavitation bubbles and further intensifies the generation of the inertial cavitation and heat accumulation so as to reduce the time required of the first stage.

Step 3) includes the following steps. The arbitrary waveform generator 1 transmits a pulse sequence with a relatively low duty cycle, which is amplified by the power amplifier 2 to a specified power. The HIFU transducer 4 is driven by the impedance matching network 3 and performs the second stage to the target tissue of sample 13 under monitoring of the monitoring and guiding system. The relatively low duty cycle (DC) range is DC<2%. The hundred-microsecond refers to a pulse duration within 100-1000 μs. Two harmonically related exciting pulses simultaneously transmitted by two arbitrary waveform generators controlled by timing sequence respectively drives the transducers after their power being amplified. At this stage, the mechanical effect of the low duty cycle pulsed focused ultrasound is mainly utilized to further disintegrate and homogenize the target tissue. The large number of cavitation nuclei generated in the first stage produce more severe transient cavitation under the action of fundamental and harmonic superposition combined with ultrasound pulses. The shear force generated by the collapse of the cavitation bubbles and boiling bubbles breaks the target tissue and achieve the tissue lesion.

Figure 1:
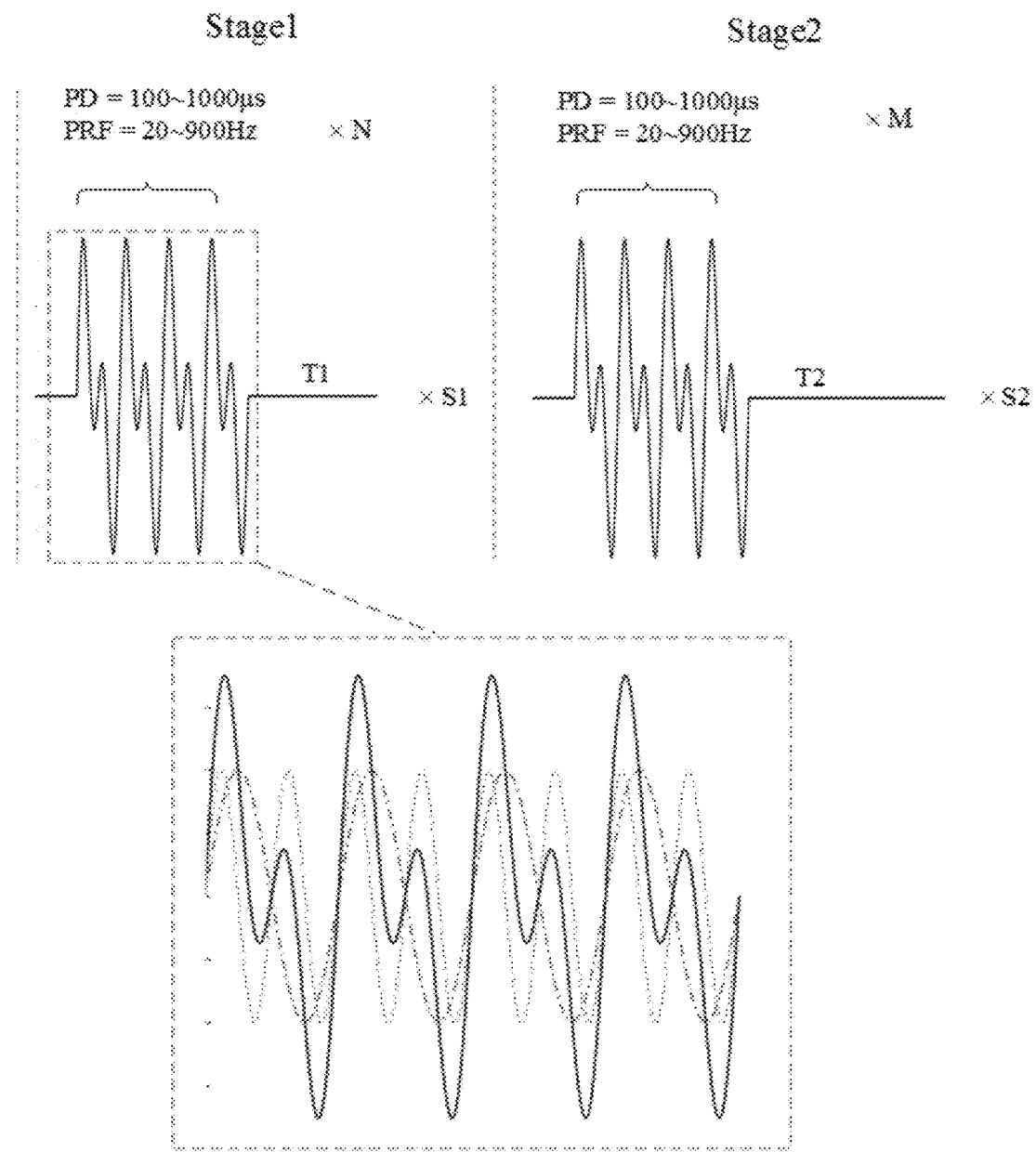
FIG. 1 shows schematic diagrams of pulse sequences used in a method for controlling a histotripsy mode using a confocal fundamental and harmonic superposition combined with hundred-microsecond ultrasound pulses according to the present invention.
Figure 2A:
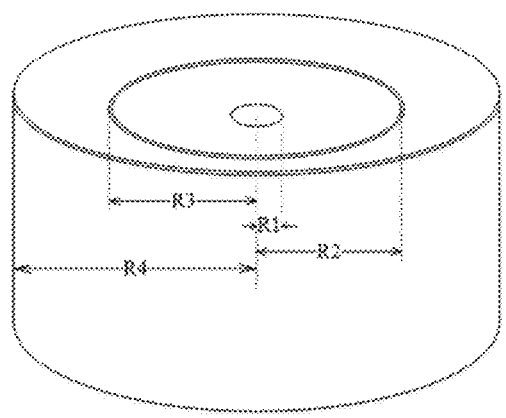
FIGS. 2(a)-(d) show schematic diagrams of HIFU transducers used in the present invention. (a) is a schematic diagram of a confocal annular split-array transducer, R1 is an inner ring inner radius, R2 is an inner ring outer radius, R3 is an outer ring inner radius, and R4 is outer ring outer radius. (b) is a schematic diagram of a confocal sectorial split-array transducer. (c) is a schematic diagram of a confocal sectorial volute split-array transducer. (d) is a schematic diagram of a confocal rectangular split-array transducer.
Figure 2B:
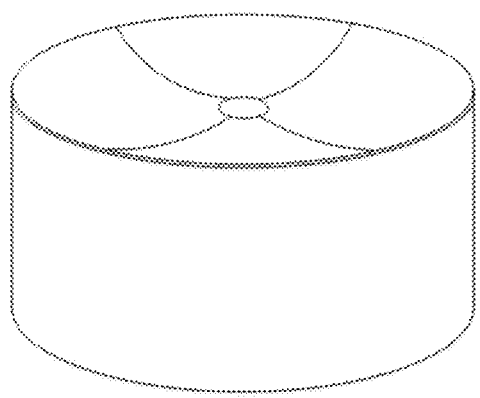
Figure 2C:
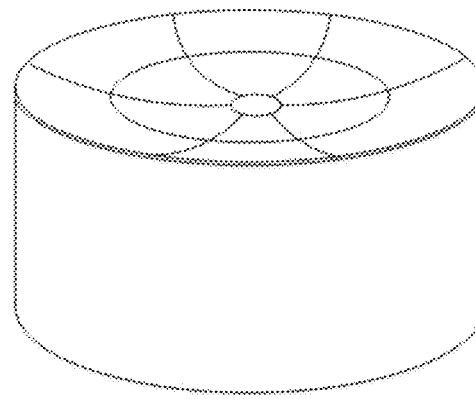
Figure 2D:
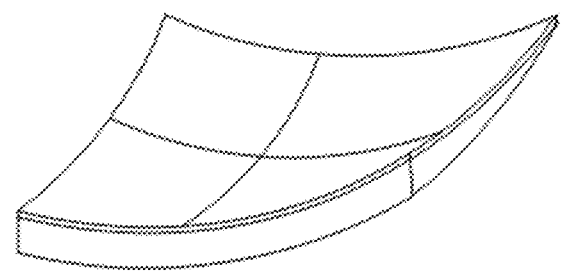

FIG. 1 shows a schematic diagram of a typical pulse sequence of the method of the present invention. The first stage includes 4-20 groups of pulse sequence with a duty cycle of 3%-10%. Each group of pulse sequence includes 50-500 single pulse trains with a pulse duration of 100-1000 μs and a pulse repetition frequency of 20-900 Hz. The second stage includes 8-30 groups of pulse sequence with a duty cycle of less than 2%. Each group of pulse sequence includes 10-100 single pulse trains with a pulse duration of 100-1000 μs and a pulse repetition frequency of 20-900 Hz. There is a off time of 300-1200 ms between each train. The off time here is mainly used to eliminate "cavitation memory" and make the formed lesion more homogeneous.

As shown in FIGS. 2(a)-(d), the transducer includes a fundamental array element and a harmonic array element. The transducer in the present invention may be a concave spherical annular split-array transducer with a hole in the center. The inner ring inner radius R1, inner ring outer radius R2, outer ring inner radius R3, outer ring outer radius R4, and focus depth can be adjusted according to the therapy protocols and the depth of the target tissue. The transducer in the present invention may also be a confocal sectorial split-array, confocal rectangular split-array or confocal sector vortex split-array transducer with a hole in the center.

In a simulation calculation of the axial acoustic pressure in the sound field in a control mode, the calculation of the axial acoustic pressure is based on the Reyleigh-Sommerfeld integral, which can be obtained by the following expression:

$$P(z) = \begin{cases} j\rho c k R_{SR} u \dfrac{e^{-(\alpha+jk)\sqrt{(z-R_{SR}+\sqrt{R_{SR}^2-R_2^2})+R_2^2}} - e^{-(\alpha+jk)\sqrt{(z-R_{SR}+\sqrt{R_{SR}^2-R_1^2})+R_1^2}}}{(z-R_{SR})(\alpha+jk)}, & z \neq R_{SR} \\ j\rho c k u \left(\sqrt{R_{SR}^2-R_1^2} - \sqrt{R_{SR}^2-R_2^2}\right)e^{-(\alpha+jk)R_{SR}}, & z = R_{SR} \end{cases} \quad (1)$$

where, $\rho$ is a propagation medium density, c is a propagation velocity, $$k = \frac{\omega}{c}$$

is the wave number, u is the vibration velocity of the surface particle of the array element, $\alpha$ is the acoustic attenuation coefficient, $R_{SR}$ is the radius of curvature of the spherical transducer, and R1 is the inner ring inner radius of the transducer, R2 is the inner ring outer radius of the transducer.

The calculation of acoustic pressure at any point in space is based on the analytical expression of the effective sound field of the spherical transducer derived by the method of projection and binomial expansion proposed by Lu et al. The formula derivation coordinate system is shown in FIG. 3. The formula is expressed as follows:

$$P = \frac{j\rho c k}{2\pi} \sum_{n=1}^{N} u_n \frac{F_n \Delta A}{R_n} e^{-(\alpha+jk)R_n} \operatorname{sinc} \frac{kx_{sn}\Delta w}{2R} \operatorname{sinc} \frac{ky_{sn}\Delta h}{2R} \quad (2)$$

in the formula, $$R_n = \sqrt{(z-z_n)^2 + (y-y_n)^2 + (x-x_n)^2} \quad (3)$$

$$F_n = \frac{R_{SR}}{\sqrt{R_{SR}^2 - (x_n^2 + y_n^2)}} \quad (4)$$

$$R_{zn}^2 = R_{SR}^2 - (x_n^2 + y_n^2) \quad (5)$$

$$x_{sn} = x + \frac{z - R_{SR}}{R_{zn}} x_n \quad (6)$$

$$y_{sn} = y + \frac{z - R_{SR}}{R_{zn}} y_n \quad (7)$$

P is the complex acoustic pressure at any point in the sound field, N is number of the sector array element of the transducer, and $u_n$ is the vibration velocity of the surface medium of the nth array element.

Figure 4:
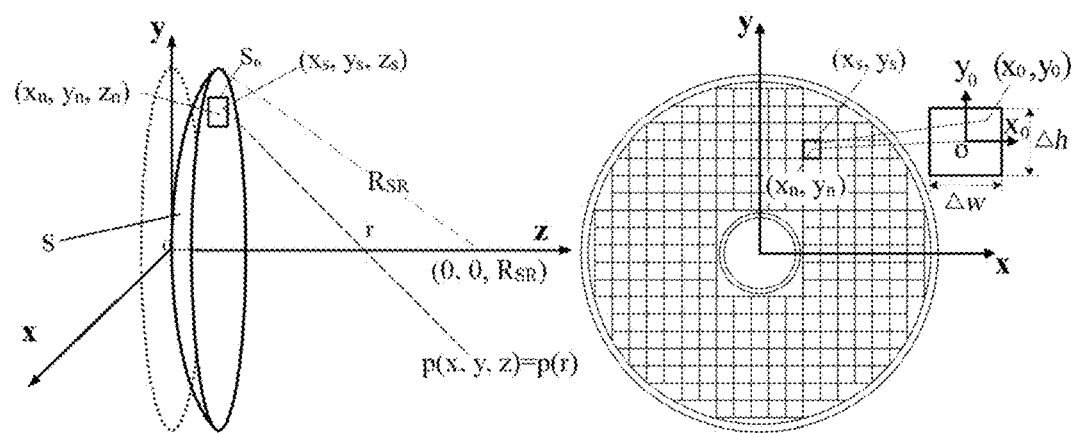
FIG. 4 is a schematic diagram showing a sound field calculation method with spherical array elements and coordinates thereof.

As shown in FIG. 4, for each annular array element of the sector split-array transducer, the array element m is first divided into N sufficiently small rectangles having the same projected region. Generally, the side lengths of the rectangles are smaller than one wavelength. The N small rectangles are superimposed with the acoustic pressures of points in the focal plane calculated by the formula (1) to obtain the acoustic pressure Pm of the sectorial array element at any point in the space, which is expressed as follows:

$$p_m = \frac{j\rho c k}{2\pi} u_m \sum_{n=1}^{N} \frac{F_n \Delta A}{R_n} e^{-(\alpha+jk)R_n} \operatorname{sinc} \frac{kx_{sn}\Delta w}{2R} \operatorname{sinc} \frac{ky_{sn}\Delta w}{2R} \quad (8)$$

The acoustic pressure at any point in the space can be obtained by superimposing the acoustic pressure generated by all the small array elements of the transducer, which is expressed as follows:

$$P = \sum_{m=1}^{M} p_m \quad (9)$$

where, $\rho$ is a propagation medium density, c is a propagation velocity, $$k = \frac{\omega}{c}$$

is the wave number, $\alpha$ is the acoustic attenuation coefficient, $x_{sn}$ is the abscissa of the nth array element, and $y_{sn}$ is the ordinate of the nth array element, $R_{SR}$ is the radius of curvature of the spherical transducer, M is the number of the sectorial array element of the transducer, and $u_m$ is the vibration velocity of the surface particle of the mth array element.

Figure 5A:
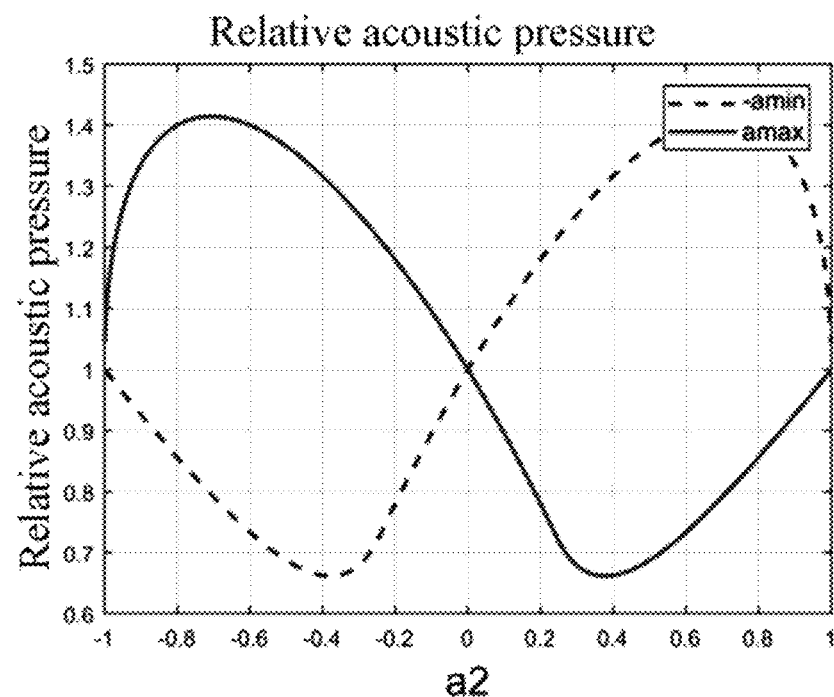
FIGS. 5(a)-(b) show a relationship between the rectified diffusion and the amplitude of the fundamental frequency acoustic pressure, and a relationship between the acoustic pressure and the amplitude of the fundamental acoustic pressure in the second-harmonic superposition mode when the total acoustic power is constant. (a) is the relationship diagram between the focal acoustic pressure and the second-harmonic acoustic pressure, where a2 is the normalized second-harmonic acoustic pressure amplitude. (b) is a relationship diagram between the normalized rectified diffusion amount and the fundamental frequency acoustic pressure, where a1 is the fundamental frequency acoustic pressure amplitude.
Figure 5B:
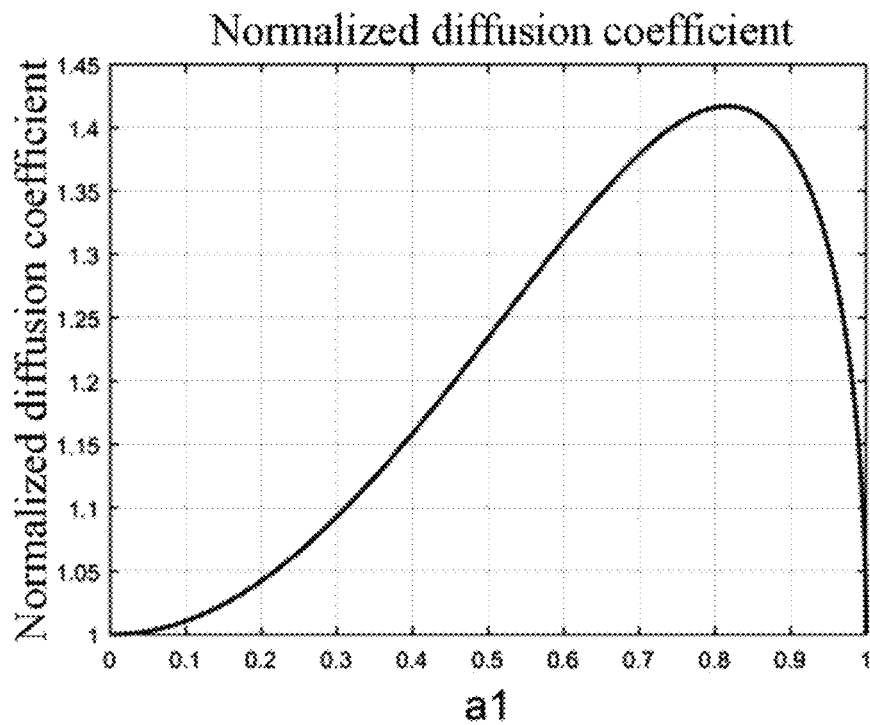
Figure 6A:
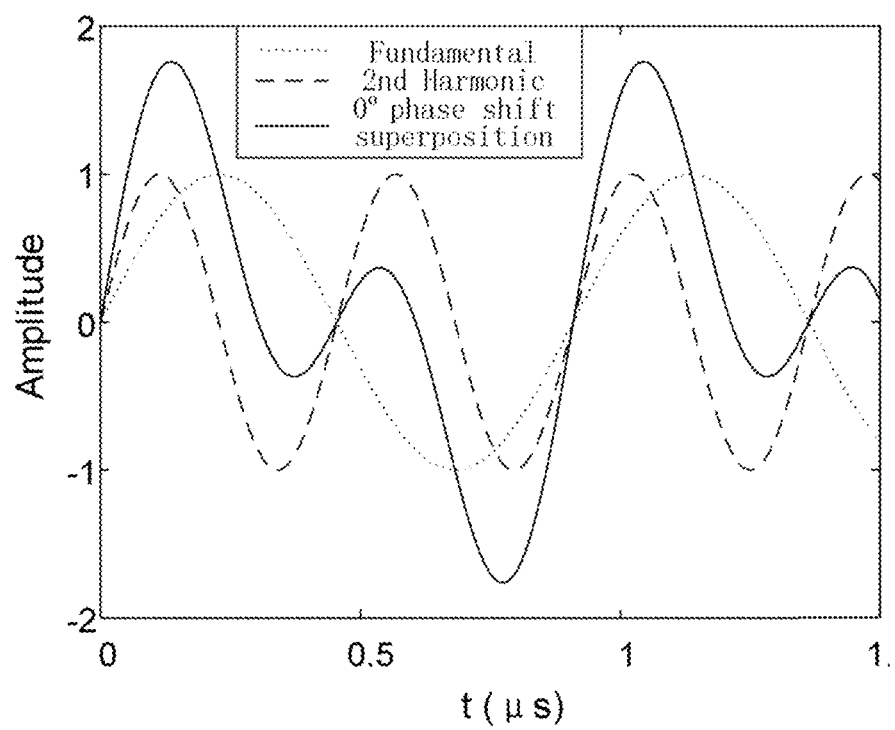
FIGS. 6(a)-(f) show timing waveform diagrams and axial sound field intensity distribution diagrams of focus acoustic pressures with different phase difference in a fundamental and second-harmonic superposition mode of a confocal annular split-array according to the present invention. (a) is a timing waveform diagram of acoustic pressure when the phase difference of the ultrasound waves transmitted by the high and low frequency rings is 0°. (b) is the axial sound field intensity distribution diagram when the phase difference of the ultrasound transmitted by the high and low frequency rings is 0°. (c) is a timing waveform diagram of acoustic pressure when the phase difference of the ultrasound transmitted by the high and low frequency rings is 90°. (d) is the axial sound field intensity distribution diagram when the phase difference of the ultrasound transmitted by the high and low frequency rings is 90°. (e) is a timing waveform diagram of acoustic pressure when the phase difference of the ultrasound transmitted by the high and low frequency rings is 135°. (f) are the axial sound field intensity distribution diagrams when the phase difference of the ultrasound transmitted by the high and low frequency rings is 135°.
Figure 6B:
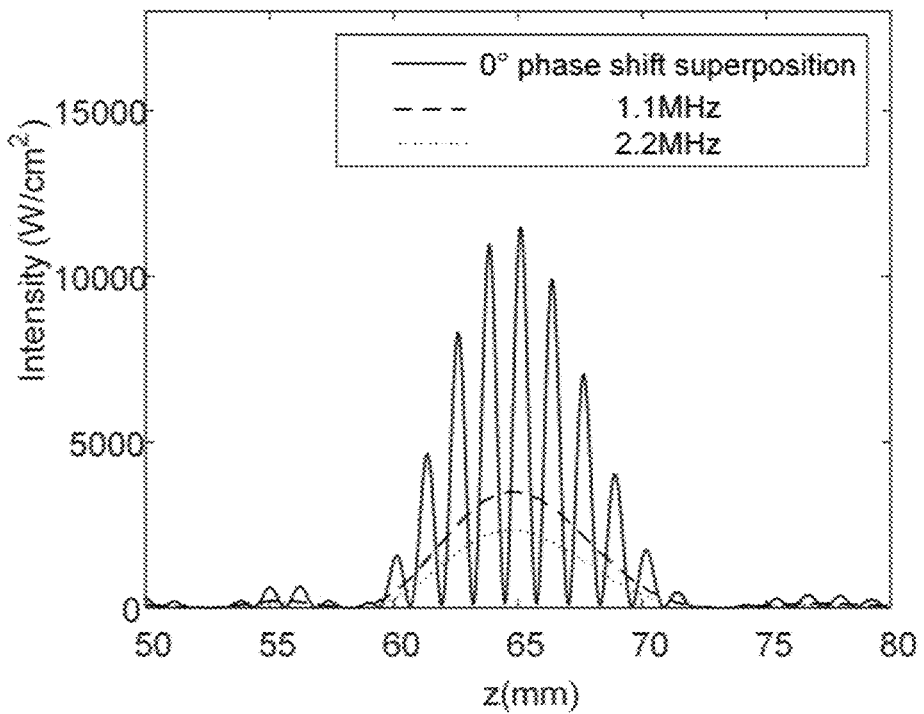
Figure 6C:
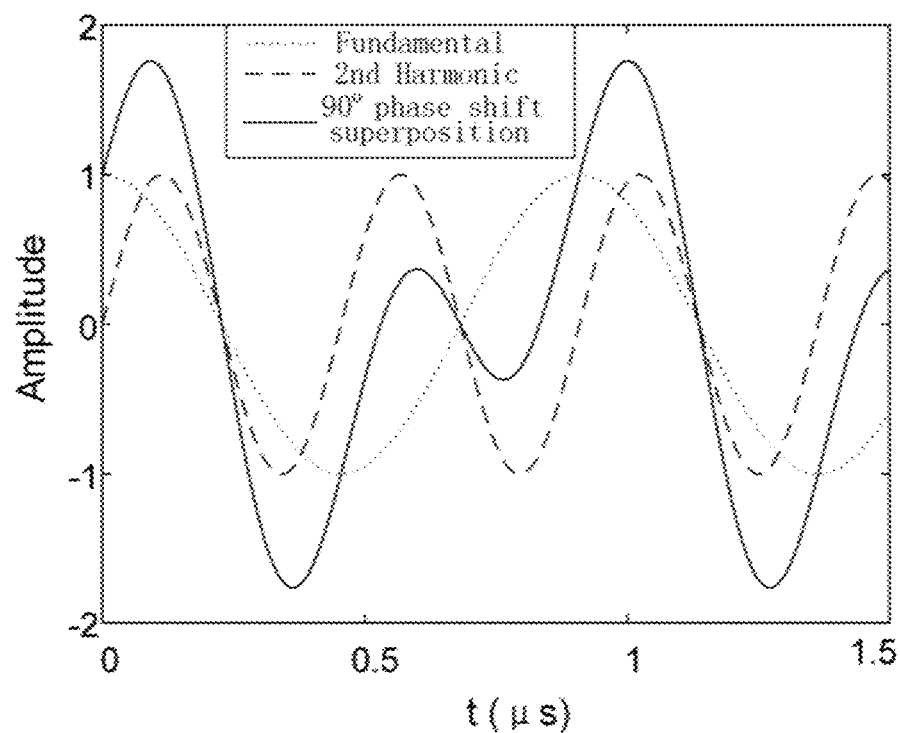
Figure 6D:
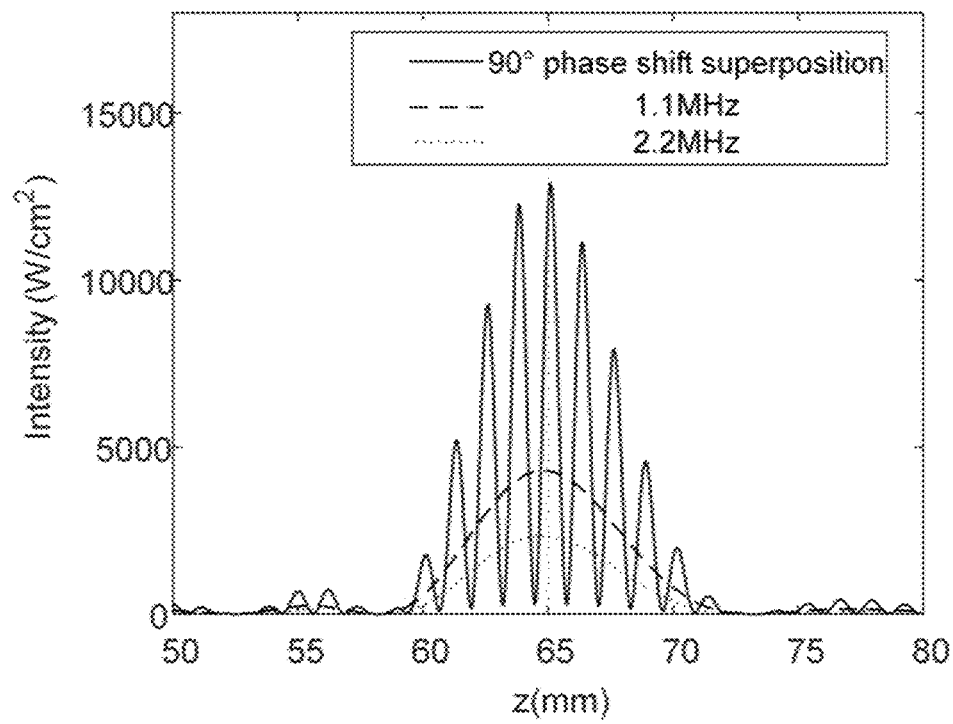
Figure 6E:
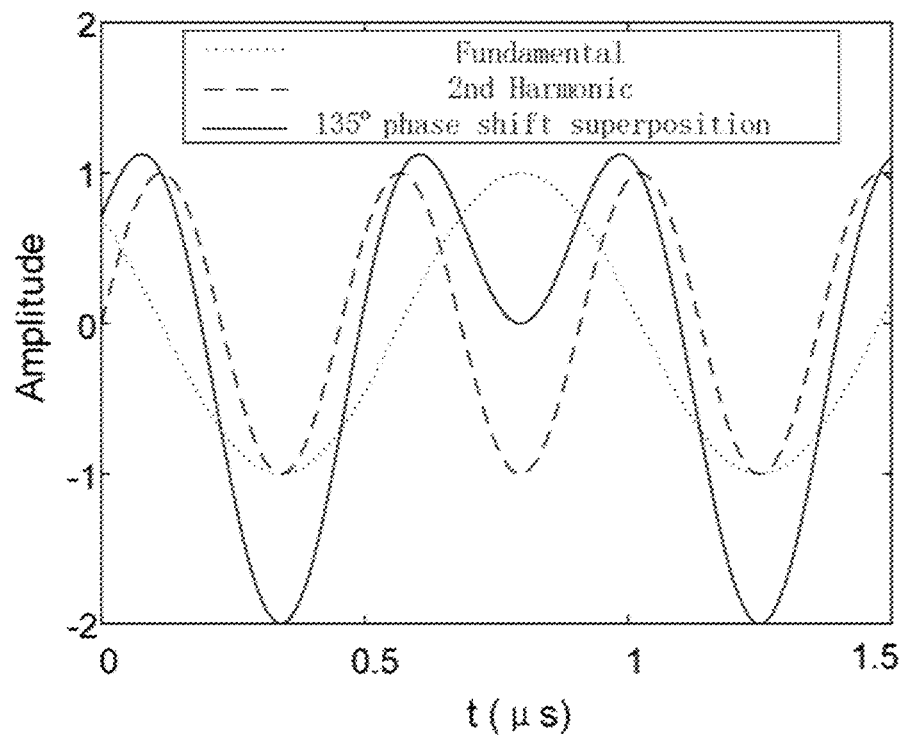
Figure 6F:
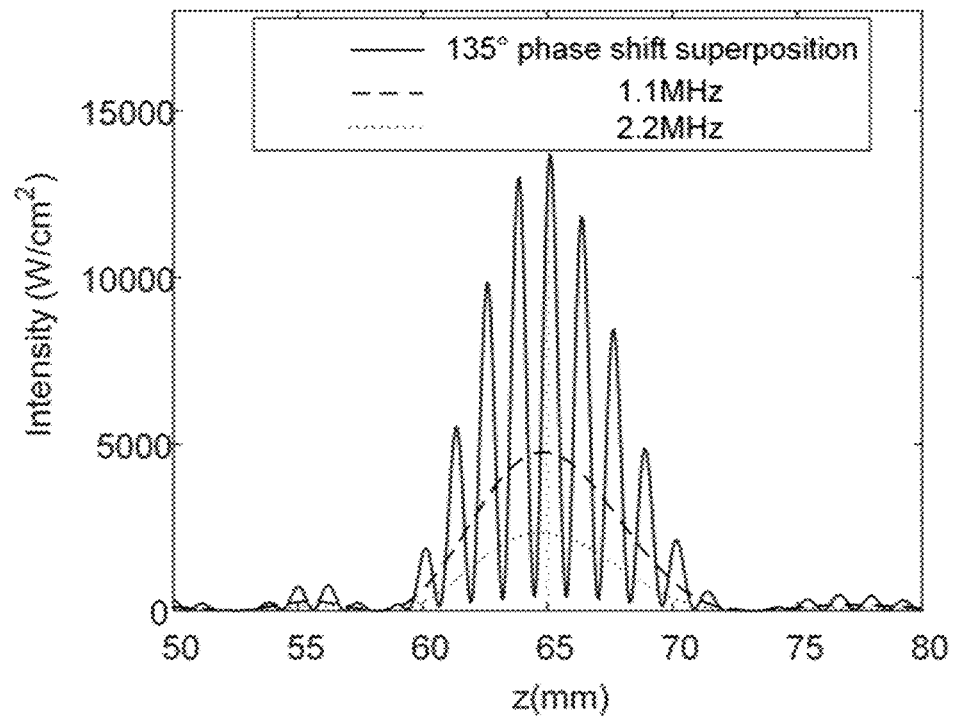

When the microbubbles nonlinearly vibrate in the sound field, the rectified diffusion of air molecules at the air-liquid interfaces of the cavitation bubbles leads to the increase of cavitation bubbles. The fundamental and harmonic superposition mode can increase the rectified diffusion rate and reduce the cavitation threshold, thereby enhancing the cavitation effect. The enhancement mechanism of the cavitation effect of the harmonic superposition mode in the present invention is mainly includes two aspects. First, FIGS. 5(a)-(b) show the simulation result that the fundamental and harmonic superposition mode can enhance the rectified diffusion effect and promote the increase of cavitation bubbles. Second, the fundamental and harmonic superposition mode enables the fundamental wave and the harmonic wave to interfere and superpose in the focal zone. The interference and superposition increases the peak negative acoustic pressure so as to more easily reach the cavitation threshold and occur the cavitation phenomenon.

FIG. 5(a) shows the relationship between the focal acoustic pressure and the second-harmonic acoustic pressure. FIG. 5(b) shows the relationship between the normalized rectified diffusion coefficient and the fundamental frequency acoustic pressure. For a single frequency, the coefficient of rectified diffusion in the same time (such as a fundamental frequency cycle) is the same regardless of the fundamental frequency or harmonic frequency. It is unhelpful to the rectified diffusion for only changing the frequency of the acoustic signal. The harmonic-frequency mode has more rectified diffusion than the single-frequency mode. When the sum of the acoustic power is constant, that is, $a^2$ is constant, it can significantly adjust the value of the rectified diffusion $F_D$ by adjusting the acoustic power of fundamental frequency and the harmonic frequency. In particular, when $$a_1 = \pm\sqrt{\frac{2}{3}}a, a_2 = \pm\sqrt{\frac{1}{3}}a,$$

that is, the acoustic power of the fundamental frequency signal is twice that of the second-harmonic signal, the relative value $F_D$ of the rectified diffusion in a single cycle reaches the maximum value in the fundamental and second-harmonic superposition mode, which is $\sqrt{2}$ times that of the single frequency mode with the same acoustic power. The increase of rectified diffusion is beneficial to the expansion of microbubbles and promotes cavitation effects, and improves the therapy efficiency of histotripsy.

FIGS. 6(a)-(f) show an interference diagram and an axial sound field intensity distribution diagram when the phase differences of ultrasound wave transmitted by the high-frequency and low-frequency rings are 0°, 90°, and 135° in the fundamental and second-harmonic superposition mode of a confocal annular split-array transducer according to the present invention. The comparison shows that the interference makes the sound energy be redistributed under the fundamental and second-harmonic superposition mode, and the sound field intensity in the focal zone under the second-harmonic superposition mode is larger than that under the single-frequency mode, thereby inducing the transient cavitation. The fundamental and second-harmonic superposition mode has great advantages in terms of improving the damage efficiency of HIFU histotripsy.

Figure 7A:
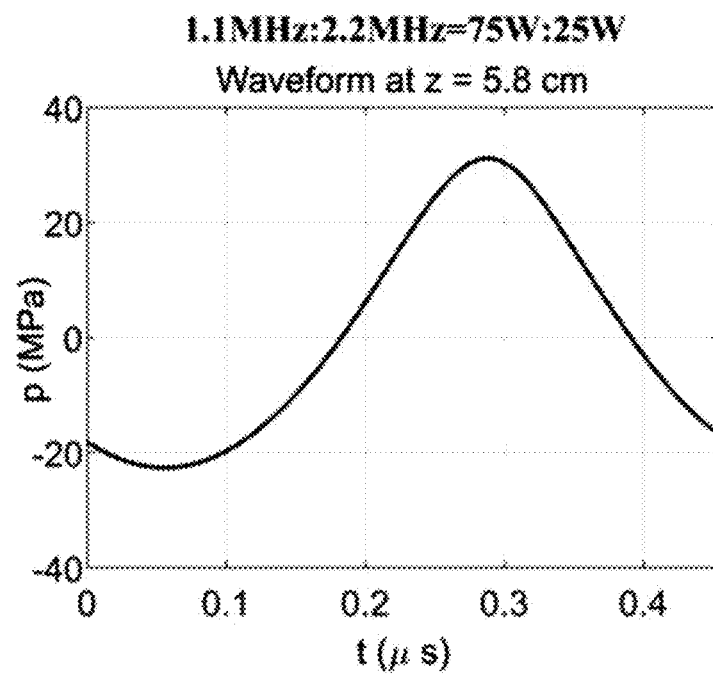
FIGS. 7(a)-(f) show timing waveform diagrams and axial acoustic pressure distribution diagrams of the focal zone when the total acoustic power is constant and the acoustic power ratios of the fundamental and harmonic waves are adjusted in the fundamental and second-harmonic superposition mode. (a) is the timing waveform diagram of focus point when the power ratio of the high to low frequency rings is 3:1. (b) is the timing waveform diagram of focus point when the power ratio of the high to low frequency rings is 1:1. (c) is the timing waveform diagram of focus point when the power ratio of the high to low frequency rings is 1:3. (d) is a distribution diagram of the axial peak positive and peak negative acoustic pressure values when the power ratio of the high to low frequency rings is 3:1. (e) is a distribution diagram of the axial peak positive and peak negative acoustic pressure values when the power ratio of the high to low frequency rings is 1:1. (f) is a distribution diagram of the axial peak positive and peak negative acoustic pressure values when the power ratio of the high to low frequency rings is 1:3.
Figure 7B:
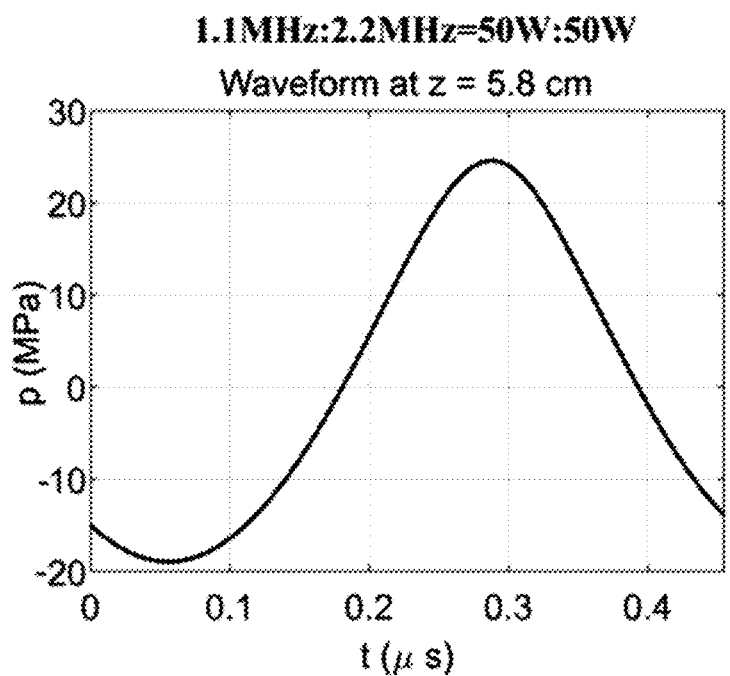
Figure 7C:
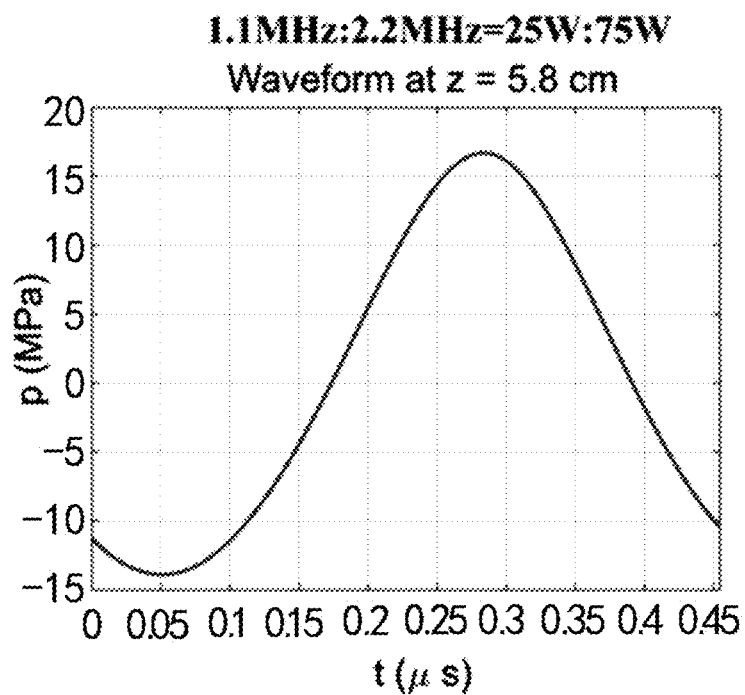
Figure 7D:
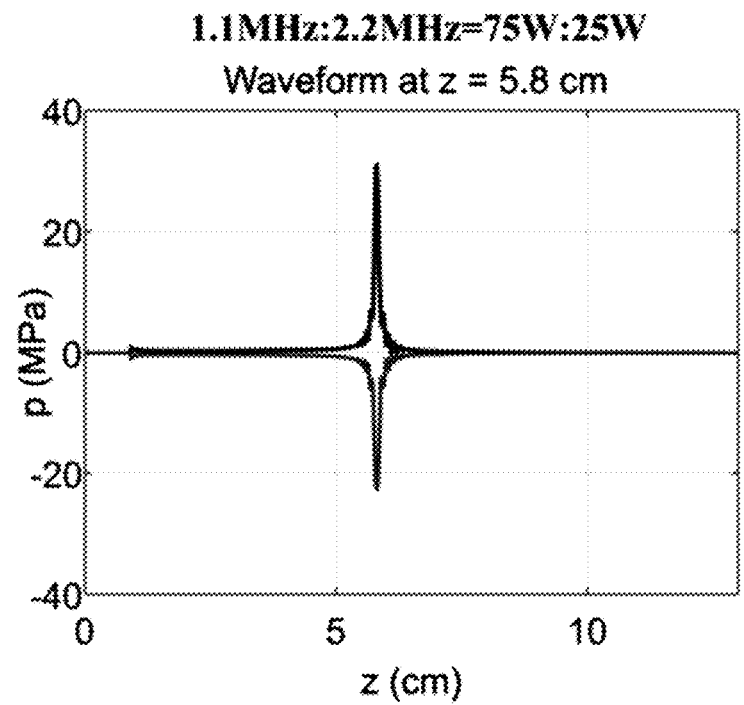
Figure 7E:
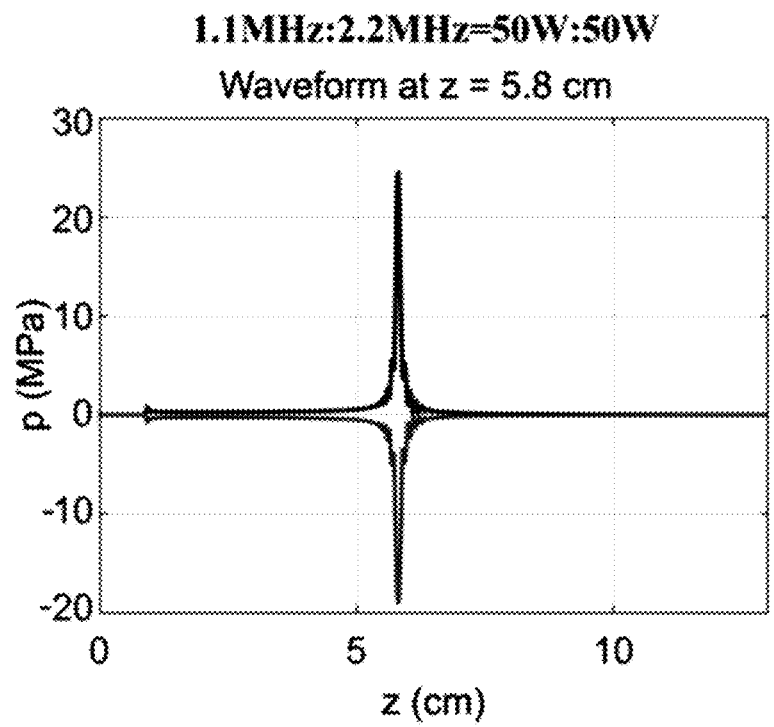
Figure 7F:
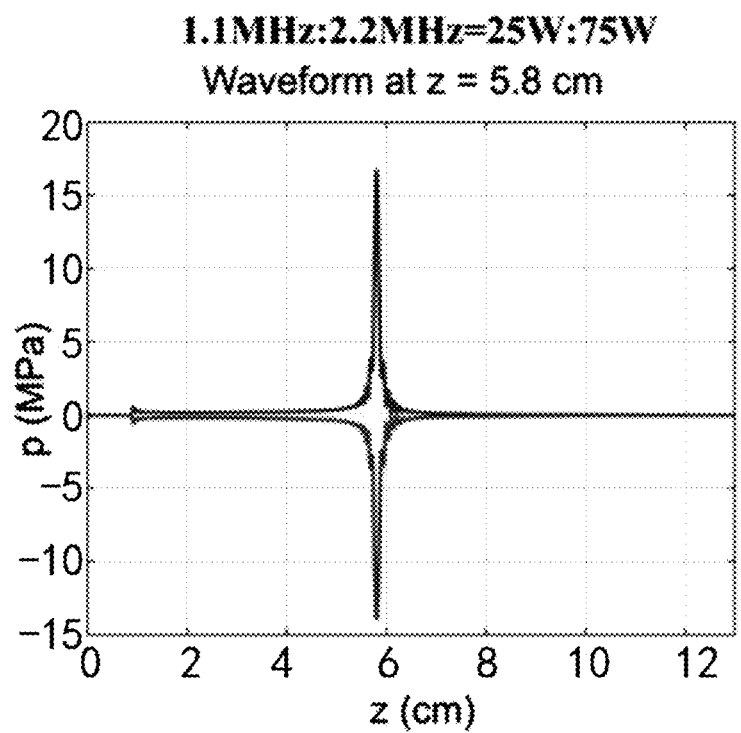
Figure 8A:
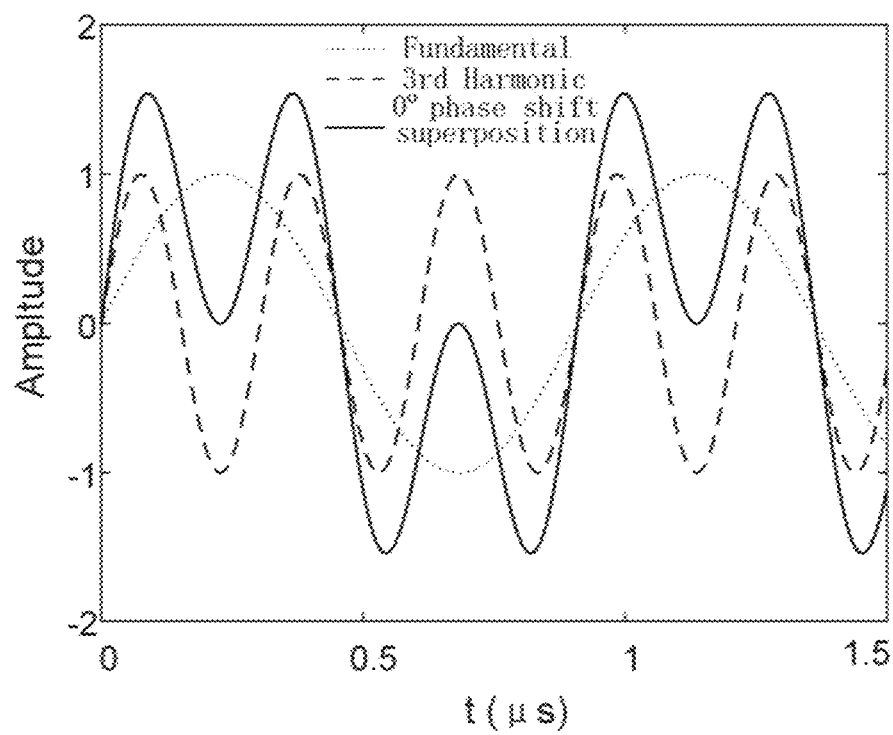
FIGS. 8(a)-(d) show timing waveform diagrams and axial sound field intensity distribution diagrams of focus acoustic pressures with different phase differences in a fundamental and third-harmonic superposition mode of a confocal annular split-array according to the present invention. (a) is a timing waveform diagram of acoustic pressure when the phase difference between the high and low frequency rings is 0°. (b) is an axial sound field intensity distribution diagram when the phase difference between the high and low frequency rings is 0°. (c) is a timing waveform diagram of acoustic pressure when the phase difference between the high and low frequency rings is 60°. (d) is an axial sound field intensity distribution diagram with the phase difference of 60°.
Figure 8B:
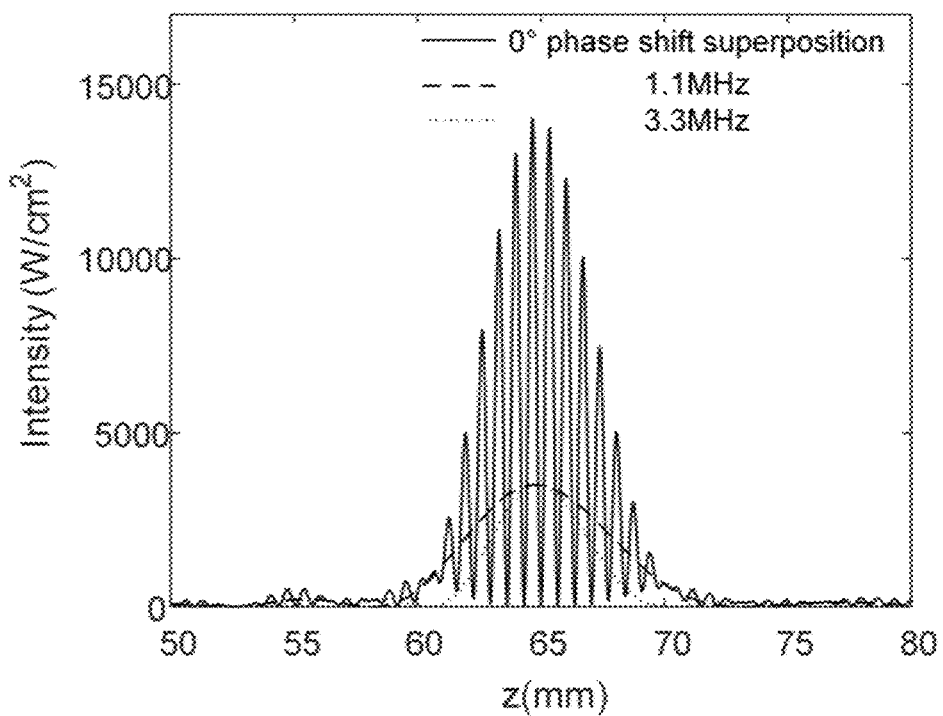
Figure 8C:
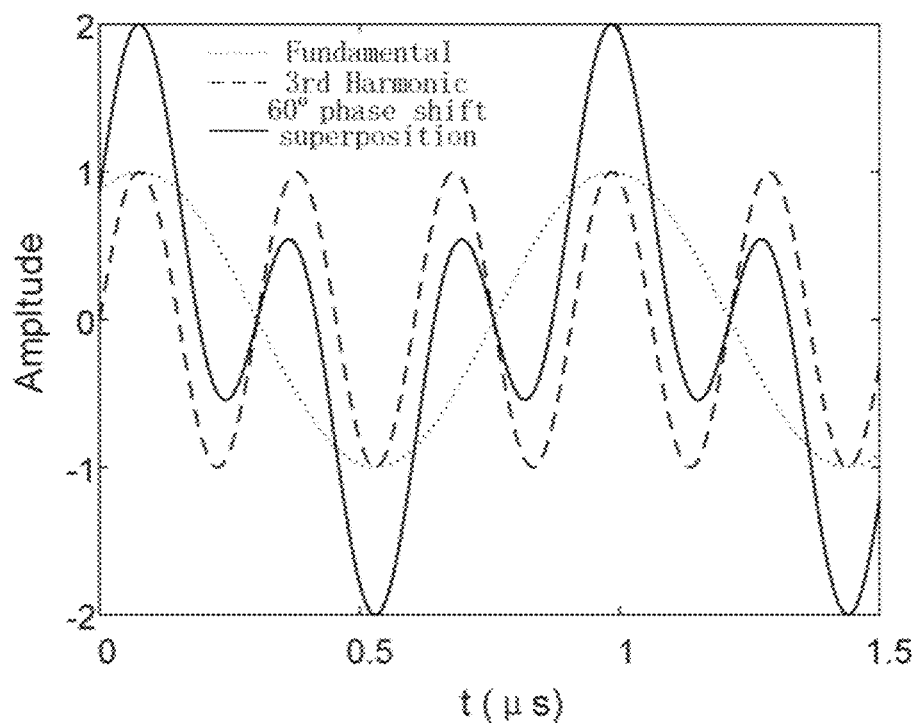
Figure 8D:
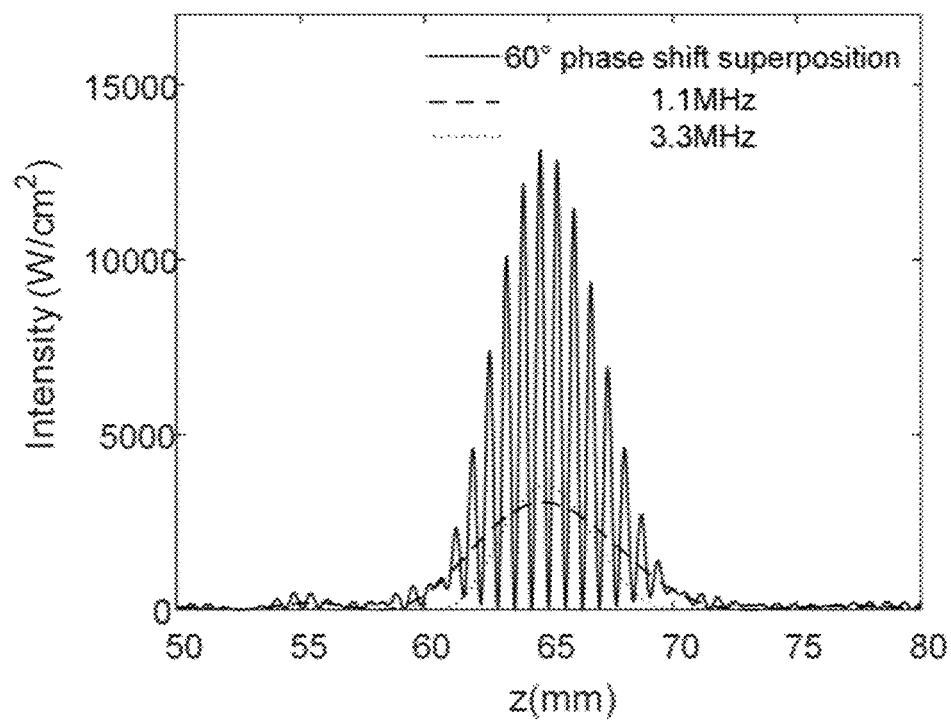
Figure 9A:
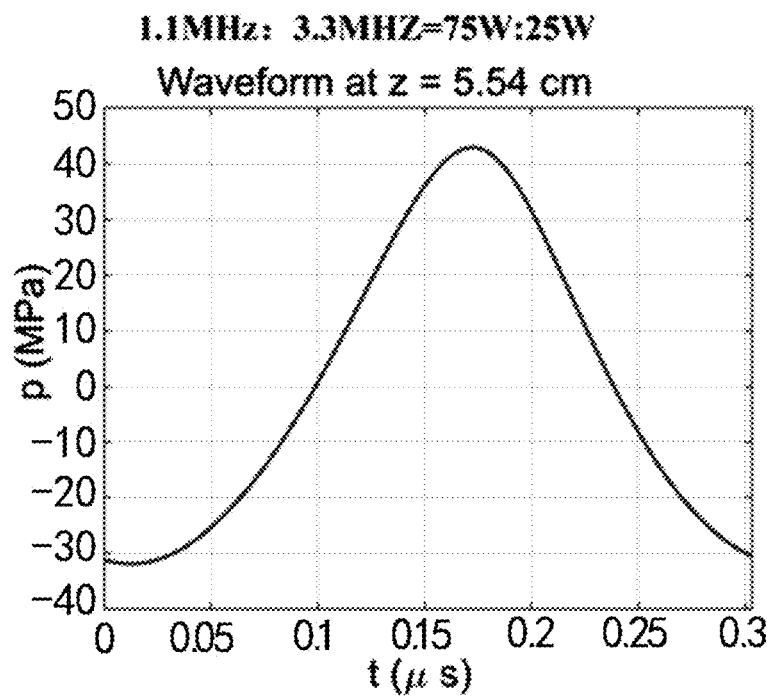
FIGS. 9(a)-(f) show timing waveform diagrams and axial acoustic pressure distribution diagrams of the focus acoustic pressures when the total acoustic power is constant and the power of the fundamental and harmonic waves are adjusted in the third-harmonic superposition mode. (a) is a timing waveform of acoustic pressure when the power ratio of the high to low frequency rings is 3:1. (b) is a timing waveform of acoustic pressure when the power ratio of the high to low frequency rings is 1:1. (c) is a timing waveform of acoustic pressure when the power ratio of the high to low frequency rings is 1:3. (d) is a distribution diagram of the axial peak positive and peak negative acoustic pressure values when the power ratio of the high to low frequency rings is 3:1. (e) is a distribution diagram of the axial peak positive and peak negative acoustic pressure values when the power ratio of the high to low frequency rings is 1:1. (f) is a distribution diagram of the axial peak positive and peak negative acoustic pressure values when the power ratio of the high to low frequency rings is 1:3.
Figure 9B:
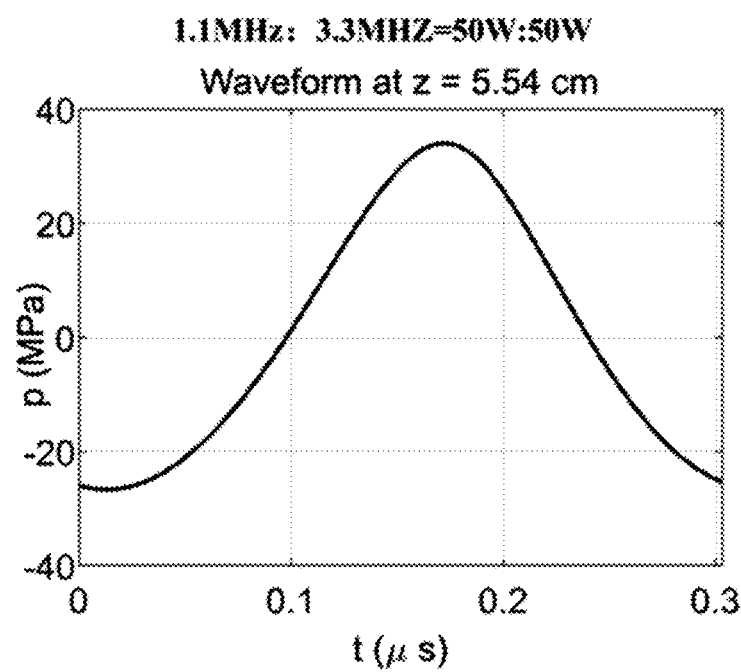
Figure 9C:
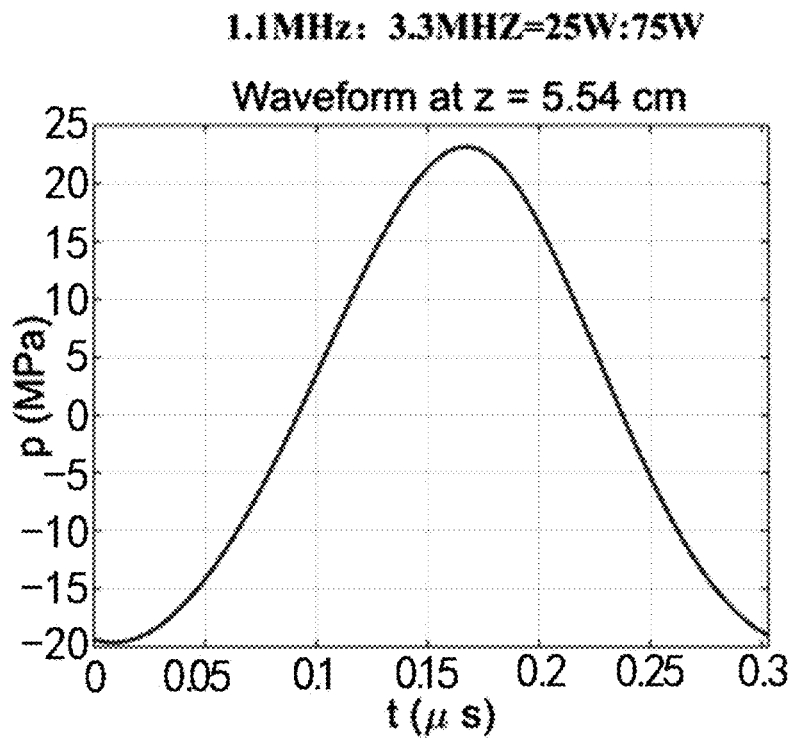
Figure 9D:
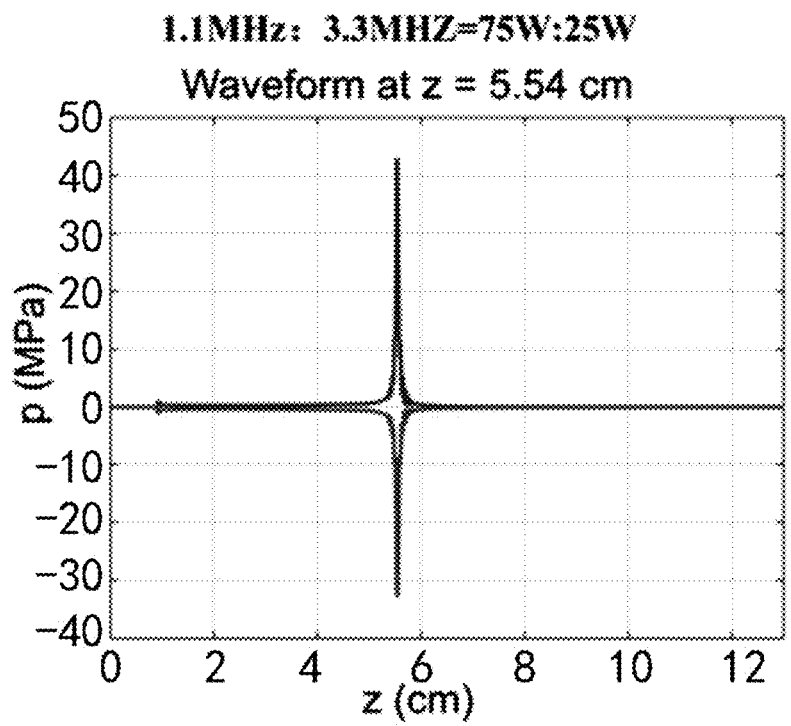
Figure 9E:
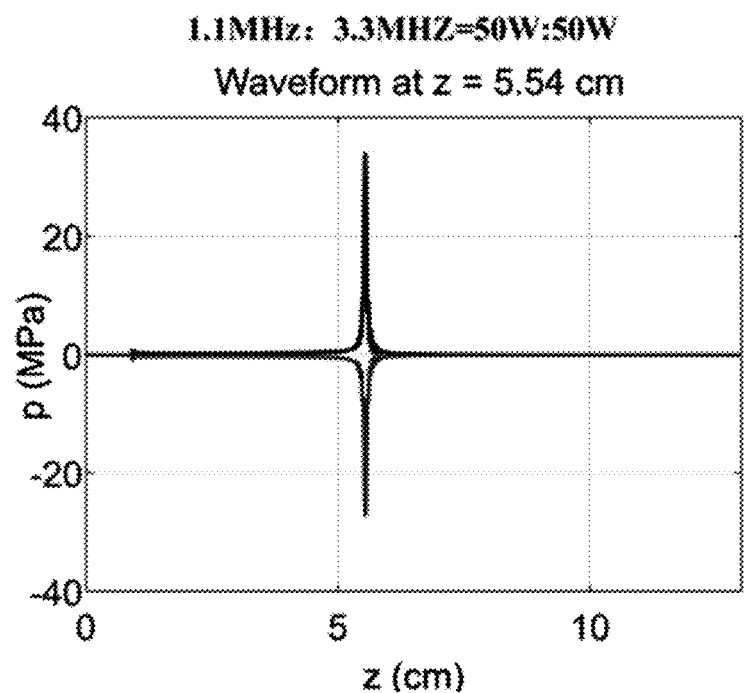
Figure 9F:
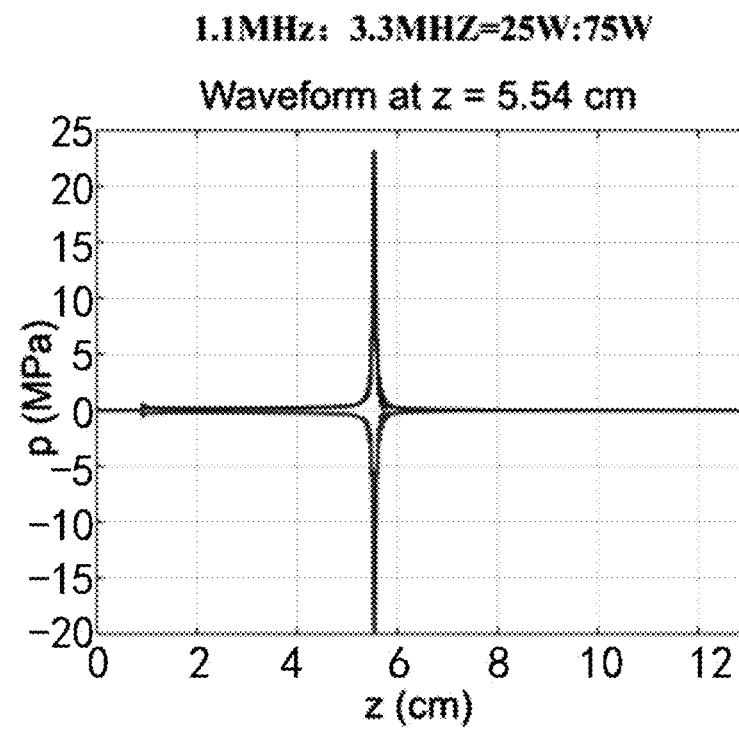

FIGS. 7(a)-(f) shows interference diagrams and axial sound field intensity distribution diagrams when the phase differences of ultrasound wave transmitted by the high-frequency and low-frequency rings are 0° and 60° in a fundamental and third-harmonic superposition mode of a confocal annular split-array transducer according to the present invention. When the phase difference between the third-harmonic and the fundamental wave is controlled to be 0° (as shown in FIG. 7(a)), the positive and negative peaks of the third-harmonic and the fundamental wave meet and superpose. The positive and negative peak acoustic pressures after the superposition reach the minimum value under the fundamental and third-harmonic superposition mode. When the phase difference between the third-harmonic and the fundamental wave is controlled to be 60° (as shown in FIG. 7(c)), the negative peaks of the third-harmonic and the fundamental wave meet and superpose. The negative peaks reach the maximum value after superposition. At the same time, the positive peaks of the third-harmonic and the fundamental wave also meet and superpose. The positive peaks after the superposition also reach the maximum value. In this way, it is beneficial to the formation of shock wave in the focal zone. It is most conducive to the collapse of transient cavitation bubbles that the negative acoustic pressure exceeds the cavitation threshold. FIG. 7(b) and FIG. 7(d) are respectively the axial sound field distribution diagrams when the phase difference is 0° and 60°. It can be seen from the comparison of FIG. 7(b) and FIG. 7(d) that the maximum sound intensity in the focal zone is larger under the 60° phase difference condition, and the width at half maximum of the acoustic pressure is also slightly wider. The above analysis shows that the focal zone is expected to obtain a more intense transient cavitation effect under the 60° phase difference condition, thereby resulting in higher HIFU damage efficiency.

In the case that the total power is kept constant, the power ratios of the different frequency array elements correspond to different acoustic pressure timing waveform diagrams and axial acoustic pressure distribution diagrams of the focal zone. The sound field simulation results of the different frequency rings of the annular array transducer under different power ratios in the method of the present invention are shown as follows.

FIGS. 8(a)-(d) show the acoustic pressure timing waveform diagrams and axial sound intensity distribution diagrams of the focal zone under different acoustic power ratios of outer ring and inner ring of the annular array transducer in the fundamental and second-harmonic superposition mode when the total power is kept constant. FIGS. 9(a)-(f) show the acoustic pressure timing waveform diagrams and axial sound intensity distribution diagrams of the focal zone under different acoustic power ratios of outer ring and inner ring of the annular array transducer in the fundamental and third-harmonic superposition mode when the total power is kept constant. It can be seen from the comparison of the simulation results that the nonlinear distortion of the waveform is more obvious with the increase of the second-harmonic acoustic power. In the second-harmonic superposition mode, the peak acoustic pressure of the waveform is increased and the cavitation threshold is more easily reached, which improves the therapy efficiency of histotripsy.

Example 1

1) A bovine-serum-albumin (BSA) polyacrylamide-gel phantom with a mass fraction of 7% was prepared, and a bovine serum albumin was added therein as an indicator of temperature change. The density of the phantom is 1.06 g/cm3, the acoustic velocity in the finished phantom is 1477±5 m/s, and the acoustic attenuation coefficient is 0.42±0.01 dB/cm.

2) The test bench was set up according to FIG. 1. The annular array transducer and the B-mode ultrasonic probe were fixed at desirable positions. An appropriate amount of deaerated water was injected into a reaction vessel. A thermostat and the ultrasonic imaging device were turned on. The phantom was adjusted to a position where the center of the phantom was in the focus of the transducer under the monitoring of the monitoring and guiding system.

3) The signal to be generated by the arbitrary waveform generator was written according to FIG. 1.

4) The excitation signal was transmitted by the arbitrary waveform generator arranged in the PC control signal excitation module and driven by the impedance matched network of the HIFU transducer after being amplified by the radio frequency power amplifier, and controlled the high-speed imaging device to perform real-time monitoring simultaneously.

Figure 10:
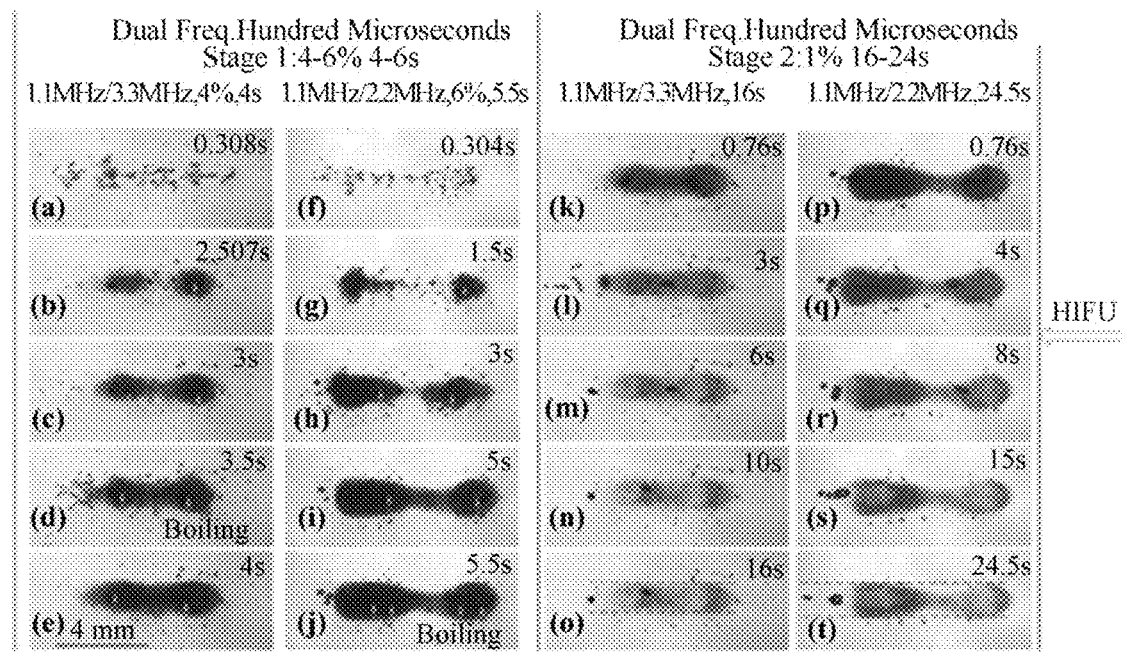
FIG. 10 shows typical results monitored by high-speed imaging when the method of the present invention is implemented in a bovine-serum-albumin acrylamide phantom. (a)-(e) show the typical results in the first stage of lesion in the fundamental and second-harmonic superposition under an action of a pulse with a high duty cycle. (f)-(j) show the typical results in the first stage of lesion in the fundamental and third-harmonic superposition under an action of a pulse with a high duty cycle. (k)-(o) show the typical results in the second stage of lesion in the fundamental and second-harmonic superposition under an action of a pulse with a low duty cycle. (p)-(t) show the typical results in the second stage of lesion in the fundamental and third-harmonic superposition under an action of a pulse with a low duty cycle.

Analysis results:

FIG. 10 shows a lesion pattern varying with the damage time in the phantom monitored by high-speed imaging. The typical results of the first and second stages in the fundamental and second-harmonic superposition mode and the fundamental and third-harmonic superposition mode are shown. In the second-harmonic superposition mode, when damage time of the first stage reaches 0.304 s, some microbubbles distributing along an axial direction can be observed. Visible boiling bubbles appear at 1.5 s. As the damage time increases, the volume and amount of the boiling bubbles increase. The liquefied region gradually becomes transparent, and the boundary becomes smooth.

The damage region are partially homogenized. (p) shows the second stage. The cavitation bubbles gather at a position in the damage region near the transducer. The subsequent pulse makes the inside of the lesion region more and more transparent, and the damage region is filled with liquid inside. The final lesion presents a regular cylindrical shape.

Example 2

1) Preparation of an acrylamide phantom liquid. Fresh porcine kidney tissue was taken, cut into a size of 5 mm×3 mm×30 mm, fixed in a phantom liquid and solidified at a normal temperature.

2) The spherical shell-shaped

An annular-array HIFU transducer and the B-mode ultrasonic probe and so on were fixed as shown in FIG. 1. An appropriate amount of degassing water was injected into the reaction vessel. The thermostat and the ultrasonic imaging device were turned on. The porcine-kidney tissue was adjusted to a position where the center of the porcine-kidney tissue is in the focus of the transducer under the monitoring of the monitoring and guiding system.

3) The signal to be generated by the arbitrary waveform generator was written according to FIG. 1.

4) The excitation signal was transmitted by the arbitrary waveform generator arranged in the PC control signal excitation module and driven by the impedance matched network of the HIFU transducer after being amplified by the radio frequency power amplifier, and controlled the high-speed imaging device to perform real-time monitoring simultaneously.

5) The lesion was observed through the B-mode ultrasonic probe after the histotripsy process is finished. Then the porcine-kidney tissue was taken out and analyzed carefully after being split. H&E staining was performed on the damaged porcine-kidney tissue. The histological results of the damaged porcine kidney tissue were observed using a high magnification microscope.

Figure 11A:
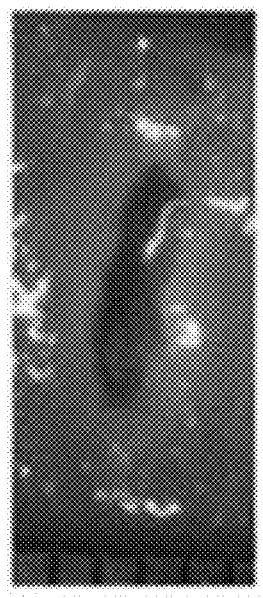
FIGS. 11(a)-(c) show the therapy results of in vitro porcine-kidney tissue under different schemes. (a)-(b) are anatomical diagrams of in vitro porcine=kidney tissue when the duty cycle is 5% in the first stage of lesion and the duty cycle is 1% in the second stage of lesion. (c) is an anatomical diagram of in vitro porcine-kidney tissue when the duty cycle is 6% in the first stage of lesion and the duty cycle is 1% in the second stage of lesion.
Figure 11B:
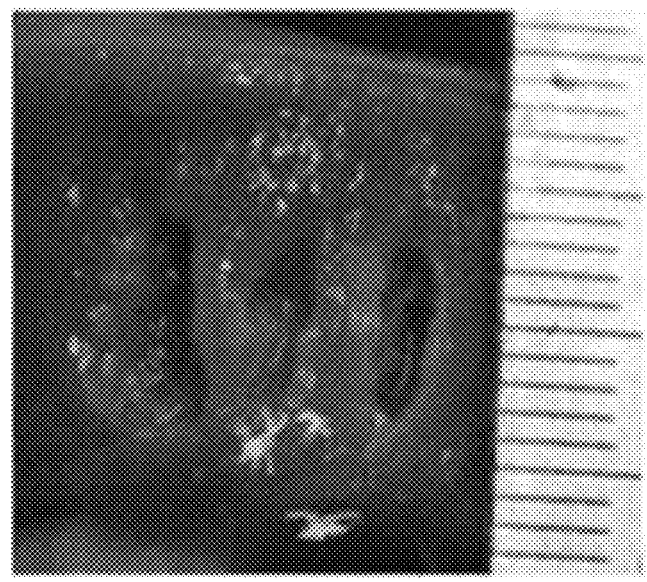
Figure 11C:
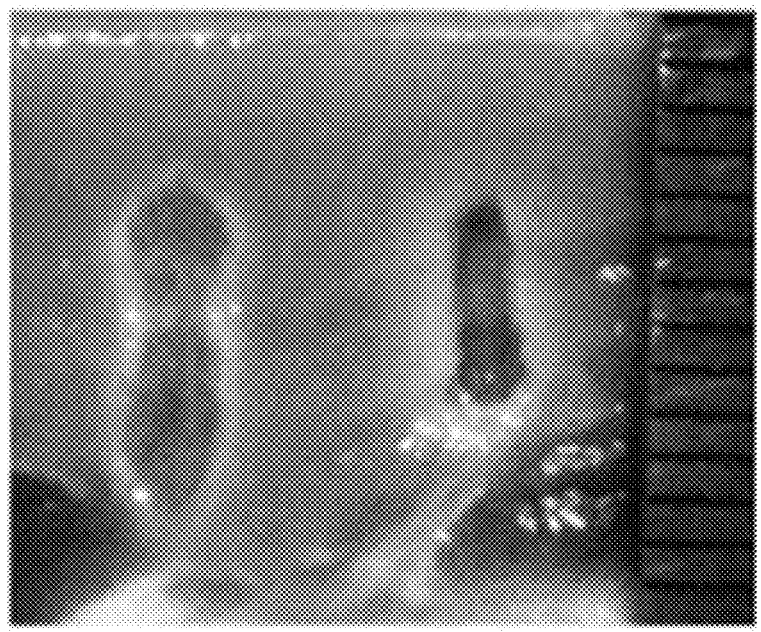
Figure 12A:
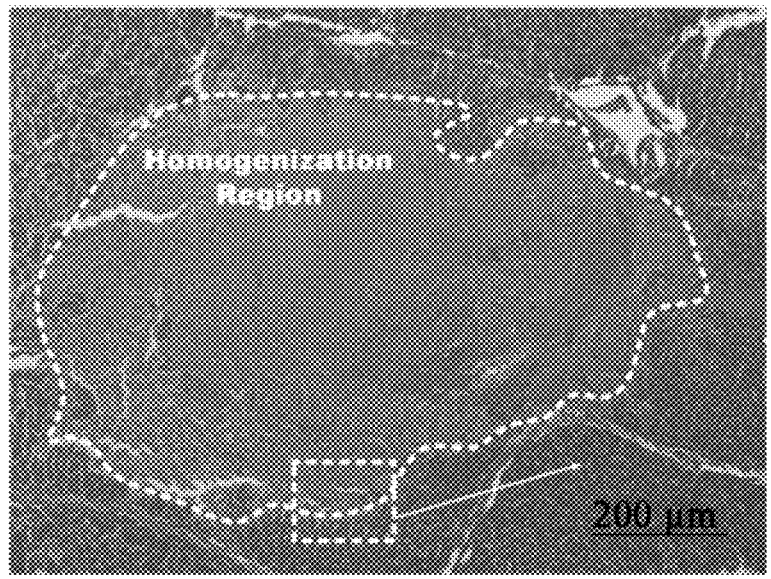
FIGS. 12(a)-(d) show the results of H&E staining of the treatment porcine-kidney tissue. (a) is a comparison diagram of homogenized tissue and normal tissue after two stages of therapy. (b) shows the enlarged lesion boundary, where the boundary between the homogenized region and the normal region is clear. (c) is an enlarged diagram of the lesion region, where the liquefied region is completely homogenized. (d) is an enlarged diagram of the normal region, where the cell structure of the normal region remains intact.
Figure 12B:
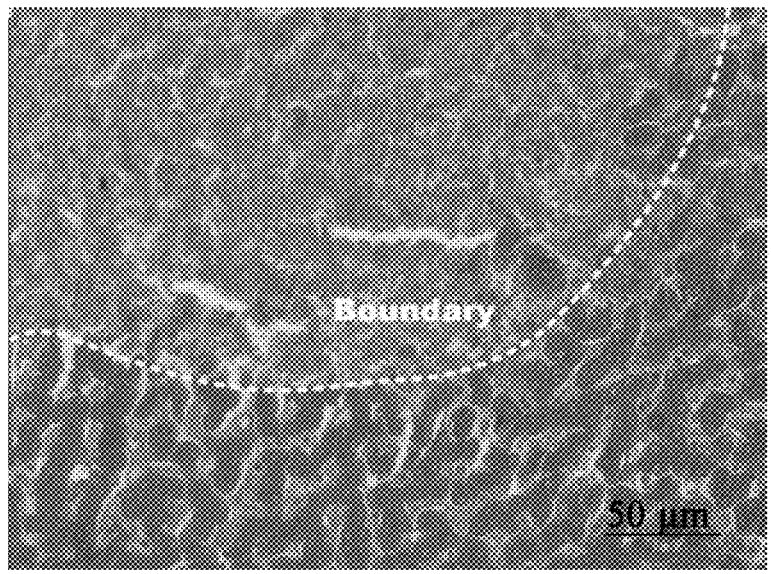
Figure 12C:
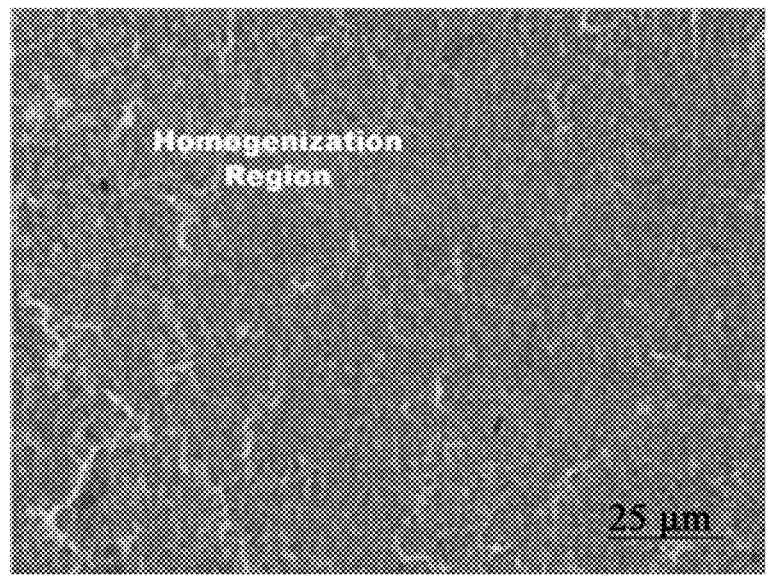
Figure 12D:
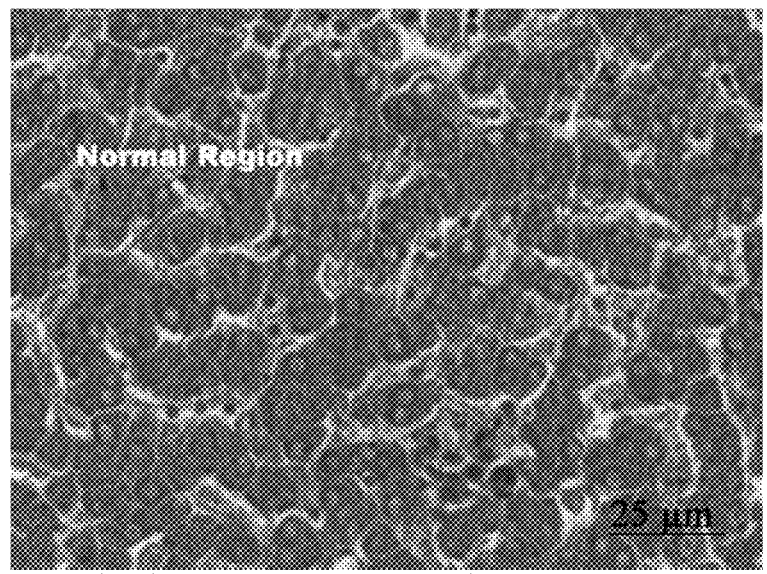

Analysis results:

FIGS. 11(a)-(c) show the results of a group of in vitro porcine kidney tissues after histotripsy. FIG. 11(a) and FIG. 11(b) show the results of the first stage of lesion when the duty cycle DC is 5%. FIG. 11(c) is the result of the first stage of lesion when the duty cycle DC is 6%. The duty cycle in the second stage is 1%. It is found that the target tissue was obviously disintegrated after the homogenized medium was washed away. The lesion presented a relatively regular cylindrical shape. Compared to FIGS. 11(a) and 11(b), the damage in FIG. 11(c) is slightly distorted, and the boundary between the damaged region and the normal region is slightly thermally coagulation due to thermal diffusion, and an obvious over-damaged region is generated, which is caused by the high duty cycle in the first stage. FIG. 12 shows the damaged porcine kidney tissue after H&E staining. FIG. 12(c) shows the tissue in the lesion region. FIG. 12(d) shows the tissue in the normal region. FIG. 12(a) shows that a clear boundary is generated between the tissues in the lesion region and normal region. As shown in FIG. 12(b), it can be clearly seen that the lesion region inside the boundary is completely homogenized and the cell structure in the normal region outside the boundary remains intact after the boundary is enlarged. Compared to the method using a hundred-microsecond pulsed-focused ultrasound by a single-frequency single-array element in both stages of lesion, the method of the present disclosure has a better damage effect.

What is claimed is:

1. A method for controlling a histotripsy using a confocal fundamental and harmonic superposition combined with hundred-microsecond ultrasound pulses comprising:
   Step 1: positioning a target tissue by a monitoring and guiding system and adjusting a position of the target tissue to a focal point of a transducer;
   Step 2: first stage: controlling the confocal fundamental and harmonic superposition combined with hundred-microsecond ultrasound pulses to form a shock wave in a focal zone; wherein a negative acoustic pressure exceeds a cavitation threshold and an inertial cavitation occurs to generate boiling bubbles and achieve partial homogenization of the target tissue;
   Step 3: second stage: controlling the confocal fundamental and harmonic superposition combined with hundred-microsecond pulsed-ultrasound sequences to simultaneously work at a target zone and further mechanically disintegrate and homogenize the target tissue; wherein the transducer comprises a fundamental array element and a harmonic array element; wherein a pulsed focused ultrasound wave transmitted by the fundamental array element is a fundamental wave and a pulsed focused ultrasound transmitted by the harmonic array element is a harmonic wave;
   wherein in step 2, an operational frequency range of the fundamental wave is 1-3 MHz, and an operational frequency range of the harmonic wave is 2-10 MHz; the first stage comprises 4-20 groups of pulse sequences with a duty cycle of 3%-10%; each group of pulse sequence comprises 50-500 single pulse trains with a pulse duration of 100-1000 µs and a pulse repetition frequency of 20-900 Hz;
   wherein in step 3, the operational frequency range of the fundamental wave is 1-3 MHz, and the operational frequency range of the harmonic wave is 2-10 MHz; the second stage of damage comprises 8-30 groups of pulse sequences with a duty cycle of less than 2%; each group of pulse sequences comprises 10-100 single pulse trains with a pulse duration of 100-1000 µs and a pulse repetition frequency of 20-900 Hz and an off time of 300-1200 ms is set between each pulse train;
   wherein the target tissue is taken from a sample of a phantom or ex vivo tissue;
   wherein in steps 2 and 3, a harmonic frequency is 2-10 times the fundamental frequency; an acoustic power of the harmonic wave is 0.1-1 time the an acoustic power of the fundamental wave; the fundamental wave and the harmonic wave have a phase difference of 0-360°, interfere and superpose in the focal zone; and
   wherein in steps 2 and 3, absolute values of negative acoustic pressures are both greater than 10 MPa and less than 15 MPa, and positive acoustic pressures produce the shockwave.

2. The method of claim 1, wherein step 1 comprises: performing an image guidance and adjusting a spatial position of the target tissue to position the target tissue at the focal point of the transducer through a probe arranged in a center of the transducer.

3. The method of claim 1, wherein in step 1, the target tissue is cut out from a normal tissue along a conformal edge of the target tissue or directly damaged according to a volume size of the target tissue.

4. The method of claim 1, wherein in steps 2 and 3, the phase differences of the fundamental wave and the harmonic wave are both 135° in a fundamental and second-harmonic superposition mode; the phase differences of the fundamental wave and the harmonic wave are both 600 in a fundamental and third-harmonic superposition mode.

5. The method of claim 1, wherein the transducer is a high intensity focused ultrasound (HIFU) transducer; the HIFU transducer having a hole at its center for placing the probe of the monitoring and guiding system, and the HIFU transducer comprising one of a confocal sectorial split-array, confocal rectangular split-array, confocal annular split-array or confocal sectorial volute split-array transducer.

* * * * *